vs009290567B2

United States Patent
Bohrmann et al.

(10) Patent No.: US 9,290,567 B2
(45) Date of Patent: *Mar. 22, 2016

(54) USE OF AN ANTI-TAU PS422 ANTIBODY FOR THE TREATMENT OF BRAIN DISEASES

(71) Applicant: Hoffmann-La Roche Inc., Nutley, NJ (US)

(72) Inventors: Bernd Bohrmann, Riehen (CH); Ulrich Goepfert, Penzberg (DE); Fiona Grueninger, Arlesheim (CH); Walter Huber, Kaiseraugst (CH); Hans-Willi Krell, Penzberg (DE); Valeria Lifke, Penzberg (DE); Olaf Mundigl, Weilheim (DE); Sonja Offner, Penzberg (DE); Laurence Ozmen, Saint Louis (FR); Michael Schraemi, Penzberg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 94 days.

This patent is subject to a terminal disclaimer.

(21) Appl. No.: 13/911,991

(22) Filed: Jun. 6, 2013

(65) Prior Publication Data

US 2013/0310541 A1 Nov. 21, 2013

Related U.S. Application Data

(63) Continuation of application No. 12/792,810, filed on Jun. 3, 2010, now Pat. No. 8,609,097.

(30) Foreign Application Priority Data

Jun. 10, 2009 (EP) .................................... 09007656
Jun. 30, 2009 (EP) .................................... 09008487

(51) Int. Cl.
*C07K 16/18* (2006.01)
*C07K 14/47* (2006.01)
*C07K 16/30* (2006.01)
*A61K 39/00* (2006.01)

(52) U.S. Cl.
CPC ............ *C07K 16/18* (2013.01); *C07K 14/4711* (2013.01); *C07K 16/3053* (2013.01); *A61K 2039/505* (2013.01); *C07K 2317/622* (2013.01); *C07K 2317/92* (2013.01); *C07K 2317/94* (2013.01); *C07K 2319/40* (2013.01); *C07K 2319/55* (2013.01)

(58) Field of Classification Search
None
See application file for complete search history.

(56) References Cited

U.S. PATENT DOCUMENTS

2002/0086009 A1  7/2002  Ishiguro et al.
2007/0280935 A1  12/2007  Bohrmann et al.

FOREIGN PATENT DOCUMENTS

WO  98/22120  5/1998

OTHER PUBLICATIONS

The Canadian Office Action, issued on May 1, 2014, in the corresponding Canadian application No. 2,762,594.
Rudikoff et al., "Single amino acid substitution altering antigen-binding specificity," Proc. Nat. Acad. Sci. USA, vol. 79, pp. 1979-1983, Mar. 1982.
Tamura et al., "Structural Correlates of an Anticarcinoma Antibody: Identification of Specificity-Determining Residues (SDRs) and Development of a Minimally Immunogenic Antibody Variant by Retention of SDRs Only," J. Immunol., vol. 164, No. 3, pp. 1432-1441, Feb. 2000.
Gong et al, "Dysregulation of Protein Phosphorylation/Dephosphorylation in Alzheimer's Disease: A Therapeutic Target," Journal of Biomedicine and Biotechnology vol. 2006, Article ID 31825, pp. 1-11.
Bussière et al, "Phosphorylated serine422 on tau proteins is a pathological epitope found in several diseases with neurofibrillary degeneration," Acta Neuropathologica, Feb. 1999, vol. 97, Issue 3, pp. 221-230.
The Japanese Office Action, issued on Sep. 10, 2013, in the corresponding Japanese application No. 2012-514380.
Hasegawa et al., "Characterization of mAb AP422, a novel phosphorylation-dependent monoclonal antibody against tau protein," FEBS Lett. Apr. 8, 1996(1):25-30.

*Primary Examiner* — Gregory S Emch

(57) ABSTRACT

An antibody binding to Tau that is phosphorylated at serine 422 (pS422), which specifically binds to phosphorylated Tau fragment of SEQ ID NO:9 and to Tau pS422, but does not bind to Tau and to phosphorylated MCAK fragment of SEQ ID NO:17. The antibody is useful in the treatment of a Tauopathy.

2 Claims, 12 Drawing Sheets

SEQUENCE LISTING

<160> NUMBER OF SEQ ID NOS: 74

<210> SEQ ID NO 1
<211> LENGTH: 112
<212> TYPE: PRT
<213> ORGANISM: Mus musculus

<400> SEQUENCE: 1

Glu Ile Val Met Thr Gln Ala Ala Pro Ser Val Pro Val Thr Pro Gly
1               5                   10                  15

Glu Ser Ala Ser Ile Ser Cys Arg Ser Asn Lys Ser Leu Leu His Ser
            20                  25                  30

Asn Gly Asn Thr Tyr Leu Cys Trp Phe Leu Gln Arg Pro Gly Gln Ser
        35                  40                  45

Pro Gln Leu Leu Ile Tyr Arg Met Ser Thr Leu Ala Pro Gly Val Pro
    50                  55                  60

Asp Arg Phe Ser Gly Ser Gly Ser Gly Thr Ala Phe Thr Leu Arg Ile
65                  70                  75                  80

Ser Arg Leu Glu Ala Glu Asp Val Gly Val Tyr Tyr Cys Met Gln His
                85                  90                  95

Ile Glu Tyr Pro Leu Thr Phe Gly Ala Gly Thr Lys Leu Glu Leu Lys
            100                 105                 110

<210> SEQ ID NO 2
<211> LENGTH: 121
<212> TYPE: PRT
<213> ORGANISM: Mus musculus

<400> SEQUENCE: 2

Glu Val Gln Leu Val Glu Ser Gly Gly Asp Leu Val Arg Pro Gly Gly
1               5                   10                  15

Ser Leu Lys Leu Ser Cys Ala Ala Ser Gly Phe Thr Phe Arg Thr Tyr
            20                  25                  30

Gly Met Ser Trp Val Arg Gln Thr Ala Asp Lys Arg Leu Glu Trp Val
        35                  40                  45

```
Ala Thr Ile Ser Ser Gly Gly Thr Tyr Thr Tyr Tyr Ala Asp Asn Val
    50                  55                  60

Arg Glu Arg Phe Thr Ile Ser Arg Asp Asn Ala Arg Asp Thr Leu Tyr
 65                  70                  75                  80

Leu Gln Met Ser Arg Leu Glu Ser Asp Asp Thr Ala Met Tyr Tyr Cys
                 85                  90                  95

Thr Arg Arg Tyr Gly Tyr Asp Gly Gly Ser Phe Asp Val Trp Gly
                100                 105                 110

Ala Gly Thr Arg Val Thr Val Ser Ser
        115                 120

<210> SEQ ID NO 3
<211> LENGTH: 16
<212> TYPE: PRT
<213> ORGANISM: Mus musculus

<400> SEQUENCE: 3

Arg Ser Asn Lys Ser Leu Leu His Ser Asn Gly Asn Thr Tyr Leu Cys
 1               5                  10                  15

<210> SEQ ID NO 4
<211> LENGTH: 7
<212> TYPE: PRT
<213> ORGANISM: Mus musculus

<400> SEQUENCE: 4

Arg Met Ser Thr Leu Ala Pro
 1               5

<210> SEQ ID NO 5
<211> LENGTH: 9
<212> TYPE: PRT
<213> ORGANISM: Mus musculus

<400> SEQUENCE: 5

Met Gln His Ile Glu Tyr Pro Leu Thr
 1               5

<210> SEQ ID NO 6
<211> LENGTH: 5
<212> TYPE: PRT
<213> ORGANISM: Mus musculus

<400> SEQUENCE: 6

Thr Tyr Gly Met Ser
 1               5

<210> SEQ ID NO 7
<211> LENGTH: 17
<212> TYPE: PRT
<213> ORGANISM: Mus musculus

<400> SEQUENCE: 7

Thr Ile Ser Ser Gly Gly Thr Tyr Thr Tyr Tyr Ala Asp Asn Val Arg
 1               5                  10                  15

Glu

<210> SEQ ID NO 8
<211> LENGTH: 12
<212> TYPE: PRT
<213> ORGANISM: Mus musculus

<400> SEQUENCE: 8
```

Arg Tyr Gly Tyr Asp Gly Gly Ser Phe Asp Val
1               5                   10

<210> SEQ ID NO 9
<211> LENGTH: 15
<212> TYPE: PRT
<213> ORGANISM: Mus musculus
<220> FEATURE:
<221> NAME/KEY: MOD_RES
<222> LOCATION: (7)..(7)
<223> OTHER INFORMATION: Phosphorylated Ser

<400> SEQUENCE: 9

Ser Ile Asp Met Val Asp Ser Pro Gln Leu Ala Thr Leu Ala Asp
1               5                   10                  15

<210> SEQ ID NO 10
<211> LENGTH: 15
<212> TYPE: PRT
<213> ORGANISM: Mus musculus

<400> SEQUENCE: 10

Ser Ile Asp Met Val Asp Ser Pro Gln Leu Ala Thr Leu Ala Asp
1               5                   10                  15

<210> SEQ ID NO 11
<211> LENGTH: 107
<212> TYPE: PRT
<213> ORGANISM: Homo sapiens

<400> SEQUENCE: 11

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 12
<211> LENGTH: 106
<212> TYPE: PRT
<213> ORGANISM: Homo sapiens

<400> SEQUENCE: 12

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

```
Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
             85                  90                  95

Glu Lys Thr Val Ala Pro Thr Glu Cys Ser
            100                 105

<210> SEQ ID NO 13
<211> LENGTH: 330
<212> TYPE: PRT
<213> ORGANISM: Homo sapiens

<400> SEQUENCE: 13

Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 14
<211> LENGTH: 330
<212> TYPE: PRT
<213> ORGANISM: Homo sapiens

<400> SEQUENCE: 14

```
Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 15
<211> LENGTH: 327
<212> TYPE: PRT
<213> ORGANISM: Homo sapiens

<400> SEQUENCE: 15

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 16
<211> LENGTH: 327
<212> TYPE: PRT
<213> ORGANISM: Homo sapiens

<400> SEQUENCE: 16

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser

```
                    35                  40                  45
Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
                100                 105                 110

Glu Phe Glu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
            325

<210> SEQ ID NO 17
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Phosphorylated Ser

<400> SEQUENCE: 17

Ile Gln Lys Gln Lys Arg Arg Ser Val Asn Ser Lys Ile Pro Ala
 1               5                  10                  15

<210> SEQ ID NO 18
<211> LENGTH: 37
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 18
aagcttgcca ccatggagac tgggctgcgc tggcttc                                    37

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ccattggtga gggtgcccga g                                                     21

<210> SEQ ID NO 20
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
aagcttgcca ccatggacay gagggccccc actc                                       34

<210> SEQ ID NO 21
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cagagtrctg ctgaggttgt aggtac                                                26

<210> SEQ ID NO 22
<211> LENGTH: 108
<212> TYPE: PRT
<213> ORGANISM: Oryctolagus cuniculus

<400> SEQUENCE: 22

Gln Ser Val Glu Glu Ser Gly Gly Arg Leu Val Thr Pro Gly Thr Pro
1               5                   10                  15

Leu Thr Leu Thr Cys Thr Val Ser Gly Leu Ser Leu Ser Ser Asn Ala
            20                  25                  30

Ile Asn Trp Val Arg Gln Ala Pro Gly Lys Gly Leu Glu Trp Ile Gly
        35                  40                  45

Tyr Ile Ser Thr Ser Gly Asn Thr Tyr Tyr Ala Ser Trp Ala Lys Gly
    50                  55                  60

Arg Phe Thr Ile Ser Lys Thr Ser Thr Val Asp Leu Lys Ile Thr
65                  70                  75                  80

Ser Pro Thr Thr Glu Asp Thr Ala Thr Tyr Phe Cys Gly Arg Gly Asp
                85                  90                  95

Leu Trp Gly Pro Gly Thr Leu Val Thr Val Ser Ser
            100                 105

<210> SEQ ID NO 23
<211> LENGTH: 10
<212> TYPE: PRT
<213> ORGANISM: Oryctolagus cuniculus
```

<400> SEQUENCE: 23

Gly Leu Ser Leu Ser Ser Asn Ala Ile Asn
1               5                   10

<210> SEQ ID NO 24
<211> LENGTH: 16
<212> TYPE: PRT
<213> ORGANISM: Oryctolagus cuniculus

<400> SEQUENCE: 24

Tyr Ile Ser Thr Ser Gly Asn Thr Tyr Tyr Ala Ser Trp Ala Lys Gly
1               5                   10                  15

<210> SEQ ID NO 25
<211> LENGTH: 3
<212> TYPE: PRT
<213> ORGANISM: Oryctolagus cuniculus

<400> SEQUENCE: 25

Gly Asp Leu
1

<210> SEQ ID NO 26
<211> LENGTH: 112
<212> TYPE: PRT
<213> ORGANISM: Oryctolagus cuniculus

<400> SEQUENCE: 26

Gln Val Leu Thr Gln Thr Ala Ser Pro Val Ser Ala Ala Val Gly Ser
1               5                   10                  15

Thr Val Thr Ile Asn Cys Gln Ala Ser Gln Ser Val Tyr Lys Asn Asn
            20                  25                  30

Tyr Leu Ala Trp Phe Gln Gln Lys Pro Gly Gln Pro Pro Lys Arg Leu
        35                  40                  45

Ile Tyr Ser Ala Ser Thr Leu Ala Ser Gly Val Ser Ser Arg Phe Lys
    50                  55                  60

Gly Ser Gly Ser Gly Thr Gln Phe Thr Leu Thr Ile Ser Asp Val Gln
65                  70                  75                  80

Cys Asp Asp Ala Ala Thr Tyr Tyr Cys Leu Gly Ser Cys Asp Ser Ser
                85                  90                  95

Ser Asn Asn Cys Val Ala Phe Gly Gly Gly Thr Glu Val Val Val Lys
            100                 105                 110

<210> SEQ ID NO 27
<211> LENGTH: 13
<212> TYPE: PRT
<213> ORGANISM: Oryctolagus cuniculus

<400> SEQUENCE: 27

Gln Ala Ser Gln Ser Val Tyr Lys Asn Asn Tyr Leu Ala
1               5                   10

<210> SEQ ID NO 28
<211> LENGTH: 7
<212> TYPE: PRT
<213> ORGANISM: Oryctolagus cuniculus

<400> SEQUENCE: 28

Ser Ala Ser Thr Leu Ala Ser
1               5

```
<210> SEQ ID NO 29
<211> LENGTH: 13
<212> TYPE: PRT
<213> ORGANISM: Oryctolagus cuniculus

<400> SEQUENCE: 29

Leu Gly Ser Cys Asp Ser Ser Asn Asn Cys Val Ala
1               5                   10

<210> SEQ ID NO 30
<211> LENGTH: 114
<212> TYPE: PRT
<213> ORGANISM: Oryctolagus cuniculus

<400> SEQUENCE: 30

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Tyr Thr
            20                  25                  30

Met Asn Trp Val Arg Gln Ala Pro Gly Lys Gly Leu Asp Trp Ile Gly
        35                  40                  45

Phe Ile Asn Ser Gly Gly Tyr Thr Ser Tyr Ala Ser Trp Thr Arg Gly
    50                  55                  60

Arg Phe Thr Ile Ser Lys Thr Ser Thr Thr Val Asp Leu Arg Ile Thr
65                  70                  75                  80

Ser Pro Thr Thr Glu Asp Thr Ala Thr Tyr Phe Cys Ala Arg Tyr Gly
                85                  90                  95

Gly Gly Ser Gly Phe Asp Leu Trp Gly Pro Gly Thr Leu Val Thr Val
            100                 105                 110

Ser Ser

<210> SEQ ID NO 31
<211> LENGTH: 10
<212> TYPE: PRT
<213> ORGANISM: Oryctolagus cuniculus

<400> SEQUENCE: 31

Gly Ile Asp Leu Ser Ser Tyr Thr Met Asn
1               5                   10

<210> SEQ ID NO 32
<211> LENGTH: 16
<212> TYPE: PRT
<213> ORGANISM: Oryctolagus cuniculus

<400> SEQUENCE: 32

Phe Ile Asn Ser Gly Gly Tyr Thr Ser Tyr Ala Ser Trp Thr Arg Gly
1               5                   10                  15

<210> SEQ ID NO 33
<211> LENGTH: 9
<212> TYPE: PRT
<213> ORGANISM: Oryctolagus cuniculus

<400> SEQUENCE: 33

Tyr Gly Gly Gly Ser Gly Phe Asp Leu
1               5

<210> SEQ ID NO 34
<211> LENGTH: 107
<212> TYPE: PRT
<213> ORGANISM: Oryctolagus cuniculus
```

<400> SEQUENCE: 34

```
Gln Val Leu Thr Gln Thr Ala Ser Ser Val Ser Ala Val Gly Gly
1               5                   10                  15

Thr Val Thr Ile Asn Cys Gln Ser Ser Gln Ser Val Tyr Asn Asn Arg
            20                  25                  30

Leu Ala Trp Tyr Gln Gln Lys Pro Gly Gln Pro Lys Leu Leu Ile
        35                  40                  45

Tyr Lys Ala Ser Thr Leu Ala Ser Gly Val Pro Ser Arg Phe Lys Gly
50                  55                  60

Ser Gly Ser Gly Thr Gln Phe Thr Leu Thr Ile Ser Asp Leu Glu Cys
65                  70                  75                  80

Asp Asp Ala Ala Thr Tyr Tyr Cys Ala Gly Gly Tyr Ile Asn Ile Phe
                85                  90                  95

Ala Phe Gly Gly Gly Thr Glu Val Val Val Lys
                100                 105
```

<210> SEQ ID NO 35
<211> LENGTH: 12
<212> TYPE: PRT
<213> ORGANISM: Oryctolagus cuniculus

<400> SEQUENCE: 35

```
Gln Ser Ser Gln Ser Val Tyr Asn Asn Arg Leu Ala
1               5                   10
```

<210> SEQ ID NO 36
<211> LENGTH: 7
<212> TYPE: PRT
<213> ORGANISM: Oryctolagus cuniculus

<400> SEQUENCE: 36

```
Lys Ala Ser Thr Leu Ala Ser
1               5
```

<210> SEQ ID NO 37
<211> LENGTH: 9
<212> TYPE: PRT
<213> ORGANISM: Oryctolagus cuniculus

<400> SEQUENCE: 37

```
Ala Gly Gly Tyr Ile Asn Ile Phe Ala
1               5
```

<210> SEQ ID NO 38
<211> LENGTH: 109
<212> TYPE: PRT
<213> ORGANISM: Oryctolagus cuniculus

<400> SEQUENCE: 38

```
Gln Ser Val Glu Glu Ser Gly Gly Arg Leu Val Thr Pro Gly Thr Pro
1               5                   10                  15

Leu Thr Leu Thr Cys Lys Val Ser Gly Phe Ser Leu Ser Ser Tyr Asp
            20                  25                  30

Met Asn Trp Val Arg Gln Ala Pro Gly Lys Gly Leu Glu Trp Val Gly
        35                  40                  45

Ala Ile Ser Thr Gly Gly Asn Thr Tyr Tyr Ala Ser Trp Ala Lys Gly
50                  55                  60

Arg Phe Thr Ile Ser Lys Thr Ser Thr Thr Val Thr Leu Thr Ile Thr
65                  70                  75                  80
```

```
Ser Pro Thr Thr Ala Asp Thr Ala Thr Tyr Phe Cys Ala Arg Gly Ser
                85                  90                  95

Ser Ile Trp Gly Pro Gly Thr Leu Val Thr Val Ser Leu
            100                 105

<210> SEQ ID NO 39
<211> LENGTH: 10
<212> TYPE: PRT
<213> ORGANISM: Oryctolagus cuniculus

<400> SEQUENCE: 39

Gly Phe Ser Leu Ser Ser Tyr Asp Met Asn
1               5                   10

<210> SEQ ID NO 40
<211> LENGTH: 16
<212> TYPE: PRT
<213> ORGANISM: Oryctolagus cuniculus

<400> SEQUENCE: 40

Ala Ile Ser Thr Gly Gly Asn Thr Tyr Tyr Ala Ser Trp Ala Lys Gly
1               5                   10                  15

<210> SEQ ID NO 41
<211> LENGTH: 4
<212> TYPE: PRT
<213> ORGANISM: Oryctolagus cuniculus

<400> SEQUENCE: 41

Gly Ser Ser Ile
1

<210> SEQ ID NO 42
<211> LENGTH: 112
<212> TYPE: PRT
<213> ORGANISM: Oryctolagus cuniculus

<400> SEQUENCE: 42

Gln Val Leu Thr Gln Thr Ala Ser Pro Val Ser Ala Ala Val Gly Ser
1               5                   10                  15

Thr Val Thr Ile Asn Cys Gln Ala Ser Gln Ser Val Tyr Lys Asn Asn
                20                  25                  30

Tyr Leu Arg Trp Tyr Gln Gln Lys Pro Gly Gln Pro Pro Lys Arg Leu
            35                  40                  45

Ile Tyr Thr Ala Ser Thr Leu Ala Ser Gly Val Ser Ser Arg Phe Lys
        50                  55                  60

Gly Ser Gly Ser Gly Thr Gln Phe Thr Leu Thr Ile Ser Asp Val Gln
65                  70                  75                  80

Cys Asp Asp Ala Ala Thr Tyr Tyr Cys Leu Gly Gly Tyr Asp Cys Asn
                85                  90                  95

Ser Ala Asp Cys Trp Ala Phe Gly Gly Gly Thr Glu Val Val Val Lys
            100                 105                 110

<210> SEQ ID NO 43
<211> LENGTH: 13
<212> TYPE: PRT
<213> ORGANISM: Oryctolagus cuniculus

<400> SEQUENCE: 43

Gln Ala Ser Gln Ser Val Tyr Lys Asn Asn Tyr Leu Arg
1               5                   10
```

<210> SEQ ID NO 44
<211> LENGTH: 7
<212> TYPE: PRT
<213> ORGANISM: Oryctolagus cuniculus

<400> SEQUENCE: 44

Thr Ala Ser Thr Leu Ala Ser
1               5

<210> SEQ ID NO 45
<211> LENGTH: 13
<212> TYPE: PRT
<213> ORGANISM: Oryctolagus cuniculus

<400> SEQUENCE: 45

Leu Gly Gly Tyr Asp Cys Asn Ser Ala Asp Cys Trp Ala
1               5                   10

<210> SEQ ID NO 46
<211> LENGTH: 108
<212> TYPE: PRT
<213> ORGANISM: Oryctolagus cuniculus

<400> SEQUENCE: 46

Gln Ser Val Glu Glu Ser Gly Gly Arg Leu Val Thr Pro Gly Thr Pro
1               5                   10                  15

Leu Thr Leu Thr Cys Thr Val Ser Gly Leu Ser Leu Ser Ser Asn Ala
            20                  25                  30

Ile Asn Trp Val Arg Gln Ala Pro Gly Lys Gly Leu Glu Trp Ile Gly
        35                  40                  45

Tyr Ile Ala Val Ser Gly Asn Thr Tyr Tyr Ala Ser Trp Ala Lys Gly
    50                  55                  60

Arg Phe Thr Ile Ser Lys Ala Ser Thr Thr Val Asp Leu Lys Met Thr
65                  70                  75                  80

Ser Pro Thr Ala Glu Asp Thr Gly Thr Tyr Phe Cys Gly Lys Ser Asn
                85                  90                  95

Ile Trp Gly Pro Gly Thr Leu Val Thr Val Ser Leu
            100                 105

<210> SEQ ID NO 47
<211> LENGTH: 10
<212> TYPE: PRT
<213> ORGANISM: Oryctolagus cuniculus

<400> SEQUENCE: 47

Gly Leu Ser Leu Ser Ser Asn Ala Ile Asn
1               5                   10

<210> SEQ ID NO 48
<211> LENGTH: 16
<212> TYPE: PRT
<213> ORGANISM: Oryctolagus cuniculus

<400> SEQUENCE: 48

Tyr Ile Ala Val Ser Gly Asn Thr Tyr Tyr Ala Ser Trp Ala Lys Gly
1               5                   10                  15

<210> SEQ ID NO 49
<211> LENGTH: 3
<212> TYPE: PRT
<213> ORGANISM: Oryctolagus cuniculus

```
<400> SEQUENCE: 49

Ser Asn Ile
1

<210> SEQ ID NO 50
<211> LENGTH: 111
<212> TYPE: PRT
<213> ORGANISM: Oryctolagus cuniculus

<400> SEQUENCE: 50

Gln Val Leu Thr Gln Thr Ala Ser Pro Val Ser Ala Ala Val Gly Ile
1               5                   10                  15

Thr Val Thr Ile Ser Cys Gln Ser Ser Gln Ser Val Arg Thr Asn Lys
            20                  25                  30

Leu Ala Trp Phe Gln Gln Lys Pro Gly Gln Pro Pro Lys Arg Leu Ile
        35                  40                  45

Tyr Ser Ala Ser Thr Leu Asp Ser Gly Val Pro Ser Arg Phe Ser Ala
    50                  55                  60

Ser Gly Ser Gly Thr Gln Phe Thr Leu Thr Ile Ser Asp Val Gln Cys
65                  70                  75                  80

Asp Asp Ala Ala Thr Tyr Tyr Cys Leu Gly Tyr Tyr Asp Cys Ser Ile
                85                  90                  95

Ala Asp Cys Val Ala Phe Gly Gly Thr Glu Val Val Val Lys
            100                 105                 110

<210> SEQ ID NO 51
<211> LENGTH: 12
<212> TYPE: PRT
<213> ORGANISM: Oryctolagus cuniculus

<400> SEQUENCE: 51

Gln Ser Ser Gln Ser Val Arg Thr Asn Lys Leu Ala
1               5                   10

<210> SEQ ID NO 52
<211> LENGTH: 7
<212> TYPE: PRT
<213> ORGANISM: Oryctolagus cuniculus

<400> SEQUENCE: 52

Ser Ala Ser Thr Leu Asp Ser
1               5

<210> SEQ ID NO 53
<211> LENGTH: 13
<212> TYPE: PRT
<213> ORGANISM: Oryctolagus cuniculus

<400> SEQUENCE: 53

Leu Gly Tyr Tyr Asp Cys Ser Ile Ala Asp Cys Val Ala
1               5                   10

<210> SEQ ID NO 54
<211> LENGTH: 108
<212> TYPE: PRT
<213> ORGANISM: Oryctolagus cuniculus

<400> SEQUENCE: 54

Gln Ser Val Glu Glu Ser Gly Gly Arg Leu Val Thr Pro Gly Thr Pro
1               5                   10                  15
```

```
Leu Thr Leu Thr Cys Thr Val Ser Gly Phe Ser Leu Ser Ser Asn Ala
             20                  25                  30

Ile Asn Trp Val Arg Gln Ala Pro Gly Lys Gly Leu Glu Trp Ile Gly
         35                  40                  45

Tyr Ile Ala Val Ser Gly Asn Thr Tyr Tyr Ala Ser Trp Ala Lys Gly
 50                  55                  60

Arg Phe Thr Ile Ser Lys Ala Ser Thr Thr Val Asp Leu Lys Met Thr
 65                  70                  75                  80

Ser Pro Thr Ala Glu Asp Thr Gly Thr Tyr Phe Cys Gly Lys Ser Asn
                 85                  90                  95

Ile Trp Gly Pro Gly Thr Leu Val Thr Val Ser Leu
                100                 105
```

<210> SEQ ID NO 55
<211> LENGTH: 10
<212> TYPE: PRT
<213> ORGANISM: Oryctolagus cuniculus

<400> SEQUENCE: 55

```
Gly Phe Ser Leu Ser Ser Asn Ala Ile Asn
 1               5                  10
```

<210> SEQ ID NO 56
<211> LENGTH: 16
<212> TYPE: PRT
<213> ORGANISM: Oryctolagus cuniculus

<400> SEQUENCE: 56

```
Tyr Ile Ala Val Ser Gly Asn Thr Tyr Tyr Ala Ser Trp Ala Lys Gly
 1               5                  10                  15
```

<210> SEQ ID NO 57
<211> LENGTH: 3
<212> TYPE: PRT
<213> ORGANISM: Oryctolagus cuniculus

<400> SEQUENCE: 57

```
Ser Asn Ile
 1
```

<210> SEQ ID NO 58
<211> LENGTH: 111
<212> TYPE: PRT
<213> ORGANISM: Oryctolagus cuniculus

<400> SEQUENCE: 58

```
Gln Val Leu Thr Gln Thr Thr Ser Pro Val Ser Ala Ala Val Gly Ser
 1               5                  10                  15

Thr Val Thr Ile Ser Cys Gln Ser Gln Ser Val Arg Thr Asn Lys
             20                  25                  30

Leu Ala Trp Phe Gln Gln Lys Pro Gly Gln Pro Pro Lys Arg Leu Ile
         35                  40                  45

Tyr Ser Ala Ser Thr Leu Asp Phe Gly Val Pro Ser Arg Phe Ser Ala
 50                  55                  60

Ser Gly Ser Gly Thr Gln Phe Thr Leu Thr Ile Ser Asp Val Gln Cys
 65                  70                  75                  80

Asp Asp Ala Ala Thr Tyr Tyr Cys Leu Gly Tyr Phe Asp Cys Ser Ile
                 85                  90                  95

Ala Asp Cys Val Ala Phe Gly Gly Gly Thr Glu Val Val Val Lys
                100                 105                 110
```

<210> SEQ ID NO 59
<211> LENGTH: 12
<212> TYPE: PRT
<213> ORGANISM: Oryctolagus cuniculus

<400> SEQUENCE: 59

Gln Ser Ser Gln Ser Val Arg Thr Asn Lys Leu Ala
1               5                   10

<210> SEQ ID NO 60
<211> LENGTH: 7
<212> TYPE: PRT
<213> ORGANISM: Oryctolagus cuniculus

<400> SEQUENCE: 60

Ser Ala Ser Thr Leu Asp Phe
1               5

<210> SEQ ID NO 61
<211> LENGTH: 13
<212> TYPE: PRT
<213> ORGANISM: Oryctolagus cuniculus

<400> SEQUENCE: 61

Leu Gly Tyr Phe Asp Cys Ser Ile Ala Asp Cys Val Ala
1               5                   10

<210> SEQ ID NO 62
<211> LENGTH: 109
<212> TYPE: PRT
<213> ORGANISM: Oryctolagus cuniculus

<400> SEQUENCE: 62

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Tyr Ser
            20                  25                  30

Ile Thr Trp Val Arg Gln Ala Pro Gly Lys Gly Leu Glu Tyr Ile Gly
        35                  40                  45

Phe Ile Gly Thr Gly Gly Ser Thr Tyr Tyr Ala Ser Trp Ala Lys Gly
    50                  55                  60

Arg Phe Thr Ile Ser Arg Thr Ser Thr Thr Val Asp Leu Lys Ile Thr
65                  70                  75                  80

Ser Pro Thr Thr Glu Asp Thr Ala Thr Tyr Phe Cys Ala Arg Gly Gly
                85                  90                  95

Asp Leu Trp Gly Pro Gly Thr Leu Val Thr Val Ser Ser
            100                 105

<210> SEQ ID NO 63
<211> LENGTH: 10
<212> TYPE: PRT
<213> ORGANISM: Oryctolagus cuniculus

<400> SEQUENCE: 63

Gly Ile Asp Leu Ser Ser Tyr Ser Ile Thr
1               5                   10

<210> SEQ ID NO 64
<211> LENGTH: 16
<212> TYPE: PRT
<213> ORGANISM: Oryctolagus cuniculus

<400> SEQUENCE: 64

Phe Ile Gly Thr Gly Gly Ser Thr Tyr Tyr Ala Ser Trp Ala Lys Gly
1               5                   10                  15

<210> SEQ ID NO 65
<211> LENGTH: 4
<212> TYPE: PRT
<213> ORGANISM: Oryctolagus cuniculus

<400> SEQUENCE: 65

Gly Gly Asp Leu
1

<210> SEQ ID NO 66
<211> LENGTH: 109
<212> TYPE: PRT
<213> ORGANISM: Oryctolagus cuniculus

<400> SEQUENCE: 66

Gln Val Leu Thr Gln Thr Ala Ser Ser Val Ser Ala Ala Val Gly Gly
1               5                   10                  15

Thr Val Thr Ile Asn Cys Gln Ser Ser Gln Asn Val Tyr Asn Asn Asn
            20                  25                  30

Lys Leu Ala Trp Phe Gln Gln Lys Pro Gly Gln Pro Pro Lys Arg Leu
        35                  40                  45

Ile Tyr Gly Ala Ser Thr Leu Ala Ser Gly Val Ser Ser Arg Phe Lys
    50                  55                  60

Gly Ser Gly Ser Gly Thr Gln Phe Thr Leu Thr Ile Ser Asp Leu Glu
65                  70                  75                  80

Cys Asp Asp Ala Ala Thr Tyr Tyr Cys Leu Gly Gly Tyr Ser Gly Asn
                85                  90                  95

Ile Tyr Thr Phe Gly Gly Gly Thr Glu Val Val Val Lys
            100                 105

<210> SEQ ID NO 67
<211> LENGTH: 13
<212> TYPE: PRT
<213> ORGANISM: Oryctolagus cuniculus

<400> SEQUENCE: 67

Gln Ser Ser Gln Asn Val Tyr Asn Asn Asn Lys Leu Ala
1               5                   10

<210> SEQ ID NO 68
<211> LENGTH: 7
<212> TYPE: PRT
<213> ORGANISM: Oryctolagus cuniculus

<400> SEQUENCE: 68

Gly Ala Ser Thr Leu Ala Ser
1               5

<210> SEQ ID NO 69
<211> LENGTH: 10
<212> TYPE: PRT
<213> ORGANISM: Oryctolagus cuniculus

<400> SEQUENCE: 69

Leu Gly Gly Tyr Ser Gly Asn Ile Tyr Thr
1               5                   10

<210> SEQ ID NO 70
<211> LENGTH: 104
<212> TYPE: PRT
<213> ORGANISM: Oryctolagus cuniculus

<400> SEQUENCE: 70

Gly Asp Pro Val Ala Pro Thr Val Leu Ile Phe Pro Pro Ala Ala Asp
1               5                   10                  15

Gln Val Ala Thr Gly Thr Val Thr Ile Val Cys Val Ala Asn Lys Tyr
            20                  25                  30

Phe Pro Asp Val Thr Val Thr Trp Glu Val Asp Gly Thr Thr Gln Thr
        35                  40                  45

Thr Gly Ile Glu Asn Ser Lys Thr Pro Gln Asn Ser Ala Asp Cys Thr
    50                  55                  60

Tyr Asn Leu Ser Ser Thr Leu Thr Leu Thr Ser Thr Tyr Asn Ser
65                  70                  75                  80

His Lys Glu Tyr Thr Cys Lys Val Thr Gln Gly Thr Thr Ser Val Val
                85                  90                  95

Gln Ser Phe Asn Arg Gly Asp Cys
            100

<210> SEQ ID NO 71
<211> LENGTH: 323
<212> TYPE: PRT
<213> ORGANISM: Oryctolagus cuniculus

<400> SEQUENCE: 71

Gly Gln Pro Lys Ala Pro Ser Val Phe Pro Leu Ala Pro Cys Cys Gly
1               5                   10                  15

Asp Thr Pro Ser Ser Thr Val Thr Leu Gly Cys Leu Val Lys Gly Tyr
            20                  25                  30

Leu Pro Glu Pro Val Thr Val Thr Trp Asn Ser Gly Thr Leu Thr Asn
        35                  40                  45

Gly Val Arg Thr Phe Pro Ser Val Arg Gln Ser Ser Gly Leu Tyr Ser
    50                  55                  60

Leu Ser Ser Val Val Ser Val Thr Ser Ser Gln Pro Val Thr Cys
65                  70                  75                  80

Asn Val Ala His Pro Ala Thr Asn Thr Lys Val Asp Lys Thr Val Ala
                85                  90                  95

Pro Ser Thr Cys Ser Lys Pro Thr Cys Pro Pro Pro Glu Leu Leu Gly
            100                 105                 110

Gly Pro Ser Val Phe Ile Phe Pro Pro Lys Pro Lys Asp Thr Leu Met
        115                 120                 125

Ile Ser Arg Thr Pro Glu Val Thr Cys Val Val Asp Val Ser Gln
    130                 135                 140

Asp Asp Pro Glu Val Gln Phe Thr Trp Tyr Ile Asn Asn Glu Gln Val
145                 150                 155                 160

Arg Thr Ala Arg Pro Pro Leu Arg Glu Gln Gln Phe Asn Ser Thr Ile
                165                 170                 175

Arg Val Val Ser Thr Leu Pro Ile Ala His Gln Asp Trp Leu Arg Gly
            180                 185                 190

Lys Glu Phe Lys Cys Lys Val His Asn Lys Ala Leu Pro Ala Pro Ile
        195                 200                 205

Glu Lys Thr Ile Ser Lys Ala Arg Gly Gln Pro Leu Glu Pro Lys Val
    210                 215                 220

```
Tyr Thr Met Gly Pro Pro Arg Glu Glu Leu Ser Ser Arg Ser Val Ser
225                 230                 235                 240

Leu Thr Cys Met Ile Asn Gly Phe Tyr Pro Ser Asp Ile Ser Val Glu
                245                 250                 255

Trp Glu Lys Asn Gly Lys Ala Glu Asp Asn Tyr Lys Thr Thr Pro Ala
            260                 265                 270

Val Leu Asp Ser Asp Gly Ser Tyr Phe Leu Tyr Asn Lys Leu Ser Val
        275                 280                 285

Pro Thr Ser Glu Trp Gln Arg Gly Asp Val Phe Thr Cys Ser Val Met
    290                 295                 300

His Glu Ala Leu His Asn His Tyr Thr Gln Lys Ser Ile Ser Arg Ser
305                 310                 315                 320

Pro Gly Lys

<210> SEQ ID NO 72
<211> LENGTH: 107
<212> TYPE: PRT
<213> ORGANISM: Mus musculus

<400> SEQUENCE: 72

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105

<210> SEQ ID NO 73
<211> LENGTH: 324
<212> TYPE: PRT
<213> ORGANISM: Mus musculus

<400> SEQUENCE: 73

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
```

```
                115                 120                 125
Thr Ile Thr Leu Thr Pro Lys Val Thr Cys Val Val Asp Ile Ser
    130                 135                 140

Lys Asp Asp Pro Glu Val Gln Phe Ser Trp Phe Val Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys

<210> SEQ ID NO 74
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 74

His His His His His His
1               5
```

USE OF AN ANTI-TAU PS422 ANTIBODY FOR THE TREATMENT OF BRAIN DISEASES

PRIORITY TO RELATED APPLICATION(S)

This application is a continuation of U.S. application Ser. No. 12/792,810, filed Jun. 3, 2010; which claims the benefit of European Patent Application No. 09007656.3, filed Jun. 10, 2009, and European Patent Application No. 09008487.2, filed Jun. 30, 2009, which are hereby incorporated by reference in its entirety.

The present invention relates to the use of an antibody which binds specifically to phosphorylated Tau fragment of SEQ ID NO:9 (pS422) for the treatment of brain diseases.

BACKGROUND OF THE INVENTION

Human Tau (Microtubule-associated protein Tau (Neurofibrillary tangle protein, Paired helical filament-Tau, PHF-Tau) is a neuronal microtubule-associated protein found predominantly in axons and functions to promote tubulin polymerization and stabilize microtubules. Six isoforms (isoform A, B, C, D, E, F, G, fetal-Tau) are found in the human brain, the longest isoform comprising 441 amino acids (isoform F, Uniprot P10636-8). Tau and its properties are also described by Reynolds, C. H. et al., J. Neurochem. 69 (1997) 191-198.

Tau, in its hyperphosphorylated form, is the major component of paired helical filaments (PHF), the building block of neurofibrillary lesions in Alzheimer's disease (AD) brain. Tau can be phosphorylated at its serine or threonine residues by several different kinases including GSK3beta, cdk5, MARK and members of the MAP kinase family.

Tauopathies are characterized by abnormal hyperphosphorylation of Tau and are according to Iqbal, K. et al. (Biochimica et Biophysica Acta (BBA) 1739 (2005) 198-210):

Alzheimer disease, including tangle-only form of the disease
  Down syndrome, adult cases
  Guam parkinsonism dementia complex
  Dementia pugilistica
  Pick disease
  Dementia with argyrophilic grains
  Fronto-temporal dementia
  Cortico-basal degeneration
  Pallido-ponto-nigral degeneration
  Progressive supranuclear palsy
  Gerstmann-Sträussler-Scheinker disease with tangles.

So far nearly 40 serine (S)/threonine (T) phosphorylation sites have been found in Tau from Alzheimer's disease brains (Hanger, D. P. et al., J. Biol. Chem 282 (2007) 23645-23654). The development of Tau pathology in Alzheimer's disease is related to it's phosphorylation state. However, most of the 40 phosphorylation sites are not associated with disease pathology since they are also found in Tau extracted from healthy, fetal brain tissue. Only a few phosphorylations are unique to the disease state and are presumably responsible for the abnormal, characteristic insolubility and aggregation that define Tau in the PHFs of Alzheimer brain (Morishima-Kawashima, M. et al., J. Biol. Chem 270 (1995) 823-829). According to Pei, J. J. et al., Journal of Alzheimer's Disease 14 (2008) 385-392, the existing literature provides limited and unclear information about which of these sites are specific to AD brains. Pei used a list of phospho-specific antibodies to Tau and measured their levels in the homogenates of the medial temporal cortex from 22 AD and 10 controls.

Bussiere, T. et al. (Acta Neuropathol. 97 (1999) 221-230) describes that phosphorylated serine 422 on Tau proteins is a pathological epitope found in several diseases with neurofibrillary degeneration. Augustinack, J. C. et al., (Acta Neuropathol 103 (2002) 26-35) describe pS422 as correlating with the severity of neuronal pathology in Alzheimer's disease. Guillozet-Bongaarts, A. (J. Neurochem 97 (2006) 1005-1014) describe the phosphorylation of Tau at S422 as being part of the maturation process of PHFs. Tau pS422 is also found in association with developing pathology in various transgenic mouse models of Alzheimer's disease. Thus, Deters, N. et al. mention in Biochem. Biophys. Res. Commun 379 (2009) 400-405 that double-transgenic Dom5/pR5 mice showed 7-fold increased numbers of hippocampal neurons that contain Tau specifically phosphorylated the pathological S422 epitope. Goetz, J. et al. (Science 293 (2001) 1491-1495) reported the appearance of Tau phosphorylated at S422 in the brains of Tau P301L transgenic mice injected with Abeta42 fibrils.

EP 2 009 104 relates to epitopes of the Tau protein which occur in a phosphorylated state in Tau protein from Alzheimer's disease PHFs and to the use of said epitopes for the generation of antibodies specifically detecting Alzheimer Tau protein. WO 2002/062851 and U.S. Pat. No. 7,446,180 relate to antibodies with a specificity to an abnormally truncated form of Tau protein and diagnostic and therapeutic aspects in relation to Alzheimer's disease and related Tauopathies.

WO 98/22120 relates to a method of treating a patient with Alzheimer's disease comprising the step of administering to the patient an antibody against phosphorylated Tau fragment of amino acids about 207 to about 222, amino acids about 224 to about 240, and amino acids about 390 to about 408. Animal studies where the phosphorylated Tau fragment 379-408 [P-Ser396,404] is used to vaccinate Tau transgenic mice are mentioned in Asuni, A. A. et al., J. Neuroscience 27 (2007) 9115-9129. US 2008/0050383 relates to methods of treating and preventing Alzheimer's Disease or other Tauopathies in a subject by administering a Tau protein fragment.

Monoclonal antibodies against Tau pS422 are described, for example, in EP 1 876 185. Polyclonal antibodies against Tau pS422 are commercially available (e.g. ProSci Inc. and Biosource International).

SUMMARY OF THE INVENTION

The invention comprises an antibody binding to Tau, phosphorylated at serine 422 (Tau pS422) that specifically binds to phosphorylated Tau fragment Ser-Ile-Asp-Met-Val-Asp-Ser($PO_3H_2$)-Pro-Gln-Leu-Ala-Thr-Leu-Ala-Asp (SEQ ID NO:9) and to Tau pS422 but does not bind to Tau or to the phosphorylated MCAK fragment of SEQ ID NO:17. The present invention also comprises pharmaceutical compositions containing such an antibody and methods for the manufacture of such antibodies and pharmaceutical compositions. The invention further provides methods for us of the antibody for the treatment of a Tauopathy.

The invention comprises an antibody binding phosphorylated Tau that specifically binds to the same epitope that Mab2.10.3 (anti-Tau pS422 antibody) binds. The present invention also comprises pharmaceutical compositions containing such an antibody and methods for the manufacture of such antibodies and pharmaceutical compositions. The invention further provides methods for us of the antibody for the treatment of a Tauopathy.

The antibody of the invention specifically binds to Tau pS422 and to aggregated (fibrillar), phosphorylated Tau. The antibody of the invention does not bind to nonphosphorylated Tau, nonphosphorylated Tau fragment of SEQ ID NO:10 nor phosphorylated MCAK fragment of SEQ ID NO:17.

In one embodiment, an antibody of the invention is an human IgG1 subtype. In a further embodiment of the invention an antibody of the invention is an human IgG4 subtype.

The invention comprises an anti-Tau pS422 antibody, which comprises
a) CDR1H of SEQ ID NO:6, CDR2H of SEQ ID NO:7, and CDR3H of SEQ ID NO:8,
b) CDR1H of SEQ ID NO:23, CDR2H of SEQ ID NO:24, and CDR3H of SEQ ID NO:25,
c) CDR1H of SEQ ID NO:31, CDR2H of SEQ ID NO:32, and CDR3H of SEQ ID NO:33,
d) CDR1H of SEQ ID NO:39, CDR2H of SEQ ID NO:40, and CDR3H of SEQ ID NO:41,
e) CDR1H of SEQ ID NO:47, CDR2H of SEQ ID NO:48, and CDR3H of SEQ ID NO:49,
f) CDR1H of SEQ ID NO:55, CDR2H of SEQ ID NO:56, and CDR3H of SEQ ID NO:57, or
g) CDR1H of SEQ ID NO:63, CDR2H of SEQ ID NO:64, and CDR3H of SEQ ID NO:65.

Preferably the antibody comprises
a) CDR1H of SEQ ID NO:6, CDR2H of SEQ ID NO:7, CDR3H of SEQ ID NO:8 and CDR1L of SEQ ID NO:3, CDR2L of SEQ ID NO:4, CDR3L of SEQ ID NO:5,
b) CDR1H of SEQ ID NO:23, CDR2H of SEQ ID NO:24, and CDR3H of SEQ ID NO:25, and CDR1L of SEQ ID NO:27, CDR2L of SEQ ID NO:28, CDR3L of SEQ ID NO:29,
c) CDR1H of SEQ ID NO:31, CDR2H of SEQ ID NO:32, and CDR3H of SEQ ID NO:33, and CDR1L of SEQ ID NO:35, CDR2L of SEQ ID NO:36, CDR3L of SEQ ID NO:37,
d) CDR1H of SEQ ID NO:39, CDR2H of SEQ ID NO:40, and CDR3H of SEQ ID NO:41, and CDR1L of SEQ ID NO:43, CDR2L of SEQ ID NO:44, CDR3L of SEQ ID NO:45,
e) CDR1H of SEQ ID NO:47, CDR2H of SEQ ID NO:48, and CDR3H of SEQ ID NO:49, and CDR1L of SEQ ID NO:51, CDR2L of SEQ ID NO:52, CDR3L of SEQ ID NO:53,
f) CDR1H of SEQ ID NO:55, CDR2H of SEQ ID NO:56, and CDR3H of SEQ ID NO:57, and CDR1L of SEQ ID NO:59, CDR2L of SEQ ID NO:60, CDR3L of SEQ ID NO:61, or
g) CDR1H of SEQ ID NO:63, CDR2H of SEQ ID NO:64, and CDR3H of SEQ ID NO:65, and CDR1L of SEQ ID NO:67, CDR2L of SEQ ID NO:68, CDR3L of SEQ ID NO:69.

Preferably the antibody comprises
a) a variable light chain of SEQ ID NO:1 and a variable heavy chain of SEQ ID NO:2,
b) a variable light chain of SEQ ID NO:26 and a variable heavy chain of SEQ ID NO:22,
c) a variable light chain of SEQ ID NO:34 and a variable heavy chain of SEQ ID NO:30,
d) a variable light chain of SEQ ID NO:42 and a variable heavy chain of SEQ ID NO:38,
e) a variable light chain of SEQ ID NO:50 and a variable heavy chain of SEQ ID NO:46,
f) a variable light chain of SEQ ID NO:58 and a variable heavy chain of SEQ ID NO:54, or
g) a variable light chain of SEQ ID NO:66 and a variable heavy chain of SEQ ID NO:62.

The invention comprises a humanized variant of an anti-Tau pS422 antibody Mab2.10.3. The invention comprises a chimeric variant of an anti-Tau pS422 antibody Mab2.10.3. The invention comprises a T-cell epitope depleted variant of an anti-Tau pS422 antibody Mab2.10.3. Mab2.10.3 has a variable light chain comprising SEQ ID NO:1 and a variable heavy chain comprising SEQ ID NO:2.

The invention comprises a humanized variant of an anti-Tau pS422 antibody Mab 005. The invention comprises a chimeric variant of an anti-Tau pS422 antibody Mab 005. The invention comprises a T-cell epitope depleted variant of an anti-Tau pS422 antibody Mab 005. Mab 005 has a variable light chain comprising SEQ ID NO:26 and a variable heavy chain comprising SEQ ID NO:22.

The invention comprises a humanized variant of an anti-Tau pS422 antibody Mab 019. The invention comprises a chimeric variant of an anti-Tau pS422 antibody Mab 019. The invention comprises a T-cell epitope depleted variant of an anti-Tau pS422 antibody Mab 019. Mab 019 has a variable light chain comprising SEQ ID NO:34 and a variable heavy chain comprising SEQ ID NO:30.

The invention comprises a humanized variant of an anti-Tau pS422 antibody Mab 020. The invention comprises a chimeric variant of an anti-Tau pS422 antibody Mab 020. The invention comprises a T-cell epitope depleted variant of an anti-Tau pS422 antibody Mab 020. Mab 020 has a variable light chain comprising SEQ ID NO:42 and a variable heavy chain comprising SEQ ID NO:38.

The invention comprises a humanized variant of an anti-Tau pS422 antibody Mab 085. The invention comprises a chimeric variant of an anti-Tau pS422 antibody Mab 085. The invention comprises a T-cell epitope depleted variant of an anti-Tau pS422 antibody Mab 085. Mab 085 has a variable light chain comprising SEQ ID NO:50 and a variable heavy chain comprising SEQ ID NO:46.

The invention comprises a humanized variant of an anti-Tau pS422 antibody Mab 086. The invention comprises a chimeric variant of an anti-Tau pS422 antibody Mab 086. The invention comprises a T-cell epitope depleted variant of an anti-Tau pS422 antibody Mab 086. Mab 086 has a variable light chain comprising SEQ ID NO:58 and a variable heavy chain comprising SEQ ID NO:54.

The invention comprises a humanized variant of an anti-Tau pS422 antibody Mab 097. The invention comprises a chimeric variant of an anti-Tau pS422 antibody Mab 097. The invention comprises a T-cell epitope depleted variant of an anti-Tau pS422 antibody Mab 097. Mab 097 has a variable light chain comprising SEQ ID NO:66 and a variable heavy chain comprising SEQ ID NO:62.

The invention comprises a chimeric, humanized or T-cell epitope depleted variant of an anti-Tau pS422 antibody comprising CDR1H of SEQ ID NO:6, CDR2H of SEQ ID NO:7, CDR3H of SEQ ID NO:8 and CDR1L of SEQ ID NO:3, CDR2L of SEQ ID NO:4, CDR3L of SEQ ID NO:5 or a variable light chain of SEQ ID NO:1 and a variable heavy chain of SEQ ID NO:2.

The invention comprises a chimeric, humanized or T-cell epitope depleted variant of an anti-Tau pS422 antibody comprising CDR1H of SEQ ID NO:23, CDR2H of SEQ ID NO:24, and CDR3H of SEQ ID NO:25, and CDR1L of SEQ ID NO:27, CDR2L of SEQ ID NO:28, CDR3L of SEQ ID NO:29, or a variable light chain of SEQ ID NO:26 and a variable heavy chain of SEQ ID NO:22.

The invention comprises a chimeric, humanized or T-cell epitope depleted variant of an anti-Tau pS422 antibody comprising CDR1H of SEQ ID NO:31, CDR2H of SEQ ID NO:32, and CDR3H of SEQ ID NO:33, and CDR1L of SEQ ID NO:35, CDR2L of SEQ ID NO:36, CDR3L of SEQ ID NO:37 or a variable light chain of SEQ ID NO:34 and a variable heavy chain of SEQ ID NO:30.

The invention comprises a chimeric, humanized or T-cell epitope depleted variant of an anti-Tau pS422 antibody comprising CDR1H of SEQ ID NO:39, CDR2H of SEQ ID NO:40, and CDR3H of SEQ ID NO:41, and CDR1L of SEQ ID NO:43, CDR2L of SEQ ID NO:44, CDR3L of SEQ ID NO:45 or a variable light chain of SEQ ID NO:42 and a variable heavy chain of SEQ ID NO:38.

The invention comprises a chimeric, humanized or T-cell epitope depleted variant of an anti-Tau pS422 antibody comprising CDR1H of SEQ ID NO:47, CDR2H of SEQ ID NO:48, and CDR3H of SEQ ID NO:49, and CDR1L of SEQ ID NO:51, CDR2L of SEQ ID NO:52, CDR3L of SEQ ID NO:53 or a variable light chain of SEQ ID NO:50 and a variable heavy chain of SEQ ID NO:46.

The invention comprises a chimeric, humanized or T-cell epitope depleted variant of an anti-Tau pS422 antibody comprising CDR1H of SEQ ID NO:55, CDR2H of SEQ ID NO:56, and CDR3H of SEQ ID NO:57, and CDR1L of SEQ ID NO:59, CDR2L of SEQ ID NO:60, CDR3L of SEQ ID NO:61 or a variable light chain of SEQ ID NO:58 and a variable heavy chain of SEQ ID NO:54.

The invention comprises a chimeric, humanized or T-cell epitope depleted variant of an anti-Tau pS422 antibody comprising CDR1H of SEQ ID NO:63, CDR2H of SEQ ID NO:64, and CDR3H of SEQ ID NO:65, and CDR1L of SEQ ID NO:67, CDR2L of SEQ ID NO:68, CDR3L of SEQ ID NO:69 or a variable light chain of SEQ ID NO:66 and a variable heavy chain of SEQ ID NO:62.

The invention comprises a method for humanizing, T-cell epitope depletion or chimerization of an anti-Tau pS422 antibody, comprising CDR1H of SEQ ID NO:6, CDR2H of SEQ ID NO:7, CDR3H of SEQ ID NO:8 and CDR1L of SEQ ID NO:3, CDR2L of SEQ ID NO:4, CDR3L of SEQ ID NO:5 or a variable light chain of SEQ ID NO:1 and a variable heavy chain of SEQ ID NO:2.

The invention comprises a method for humanizing, T-cell epitope depletion or chimerization of an anti-Tau pS422 antibody, comprising CDR1H of SEQ ID NO:6, CDR2H of SEQ ID NO:7, CDR3H of SEQ ID NO:8 and CDR1L of SEQ ID NO:3, CDR2L of SEQ ID NO:4, CDR3L of SEQ ID NO:5 or a variable light chain of SEQ ID NO:1 and a variable heavy chain of SEQ ID NO:2.

The invention comprises a method for humanizing, T-cell epitope depletion or chimerization of an anti-Tau pS422 antibody, comprising CDR1H of SEQ ID NO:23, CDR2H of SEQ ID NO:24, and CDR3H of SEQ ID NO:25, and CDR1L of SEQ ID NO:27, CDR2L of SEQ ID NO:28, CDR3L of SEQ ID NO:29, or a variable light chain of SEQ ID NO:26 and a variable heavy chain of SEQ ID NO:22.

The invention comprises a method for humanizing, T-cell epitope depletion or chimerization of an anti-Tau pS422 antibody, comprising CDR1H of SEQ ID NO:31, CDR2H of SEQ ID NO:32, and CDR3H of SEQ ID NO:33, and CDR1L of SEQ ID NO:35, CDR2L of SEQ ID NO:36, CDR3L of SEQ ID NO:37 or a variable light chain of SEQ ID NO:34 and a variable heavy chain of SEQ ID NO:30.

The invention comprises a method for humanizing, T-cell epitope depletion or chimerization of an anti-Tau pS422 antibody, comprising CDR1H of SEQ ID NO:39, CDR2H of SEQ ID NO:40, and CDR3H of SEQ ID NO:41, and CDR1L of SEQ ID NO:43, CDR2L of SEQ ID NO:44, CDR3L of SEQ ID NO:45 or a variable light chain of SEQ ID NO:42 and a variable heavy chain of SEQ ID NO:38.

The invention comprises a method for humanizing, T-cell epitope depletion or chimerization of an anti-Tau pS422 antibody, comprising CDR1H of SEQ ID NO:47, CDR2H of SEQ ID NO:48, and CDR3H of SEQ ID NO:49, and CDR1L of SEQ ID NO:51, CDR2L of SEQ ID NO:52, CDR3L of SEQ ID NO:53 or a variable light chain of SEQ ID NO:50 and a variable heavy chain of SEQ ID NO:46.

The invention comprises a method for humanizing, T-cell epitope depletion or chimerization of an anti-Tau pS422 antibody, comprising CDR1H of SEQ ID NO:55, CDR2H of SEQ ID NO:56, and CDR3H of SEQ ID NO:57, and CDR1L of SEQ ID NO:59, CDR2L of SEQ ID NO:60, CDR3L of SEQ ID NO:61 or a variable light chain of SEQ ID NO:58 and a variable heavy chain of SEQ ID NO:54.

The invention comprises a method for humanizing, T-cell epitope depletion or chimerization of an anti-Tau pS422 antibody, comprising CDR1H of SEQ ID NO:63, CDR2H of SEQ ID NO:64, and CDR3H of SEQ ID NO:65, and CDR1L of SEQ ID NO:67, CDR2L of SEQ ID NO:68, CDR3L of SEQ ID NO:69 or a variable light chain of SEQ ID NO:66 and a variable heavy chain of SEQ ID NO:62.

In one embodiment the antibody binding to Tau pS422 and having the above mentioned amino acid sequences and amino acid sequence fragments is of human IgG1 subtype. In another embodiment the antibody binding to Tau pS422 and having the above mentioned amino acid sequences and amino acid sequence fragments is of human IgG4 subtype.

A further embodiment of the invention is a pharmaceutical composition comprising an antibody according to the invention.

A further embodiment of the invention is the use of an antibody according to the invention for the manufacture of a pharmaceutical composition.

A further embodiment of the invention is the use of an antibody according to the invention for the treatment a Tauopathy selected from the group consisting of Alzheimer disease (AD), including tangle-only form of the disease, Down syndrome, (adult cases), Guam parkinsonism dementia complex, Dementia pugilistica, Pick disease, Dementia with argyrophilic grains, Fronto-temporal dementia, Cortico-basal degeneration, Pallido-ponto-nigral degeneration, Progressive supranuclear palsy, and Gerstmann-Sträussler-Scheinker disease with tangles.

A further embodiment of the invention is a method for the manufacture of a pharmaceutical composition comprising an antibody according to the invention.

A further embodiment of the invention is a nucleic acid encoding a heavy chain variable domain and/or a light chain variable domain of an antibody according to the invention.

The invention further provides expression vectors comprising a nucleic acid according to the invention capable of expressing said nucleic acid in a prokaryotic or eukaryotic host cell, and host cells containing such vectors for the recombinant production of such an antibody.

The invention further comprises a prokaryotic or eukaryotic host cell comprising a vector according to the invention.

The invention further comprises a method for the production of a recombinant human or humanized antibody according to the invention, which comprises expressing a nucleic acid according to the invention in a prokaryotic or eukaryotic host cell and recovering said antibody from said cell or the cell culture supernatant. The invention further comprises the antibody obtainable by such a recombinant method.

The invention further comprises a method for the selection of a monoclonal antibody according to the invention, in which comprises providing a number of monoclonal antibodies binding to Tau pS422, determining the specifical binding of said antibodies to phosphorylated Tau fragment of SEQ ID NO:9, to Tau and to phosphorylated MCAK fragment of SEQ ID NO:17, and selecting an antibody with a specific binding to said phosphorylated Tau fragment of at least 10,000-fold compared to its binding to Tau, and with a specific binding to said phosphorylated. Tau fragment of at least 100-fold compared to its binding to phosphorylated MCAK fragment Ile-Gln-Lys-Gln-Lys-Arg-Arg-Ser($PO_3H_7$)-Val-Asn-Ser-Lys-Ile-Pro-Ala (SEQ ID NO:17).

The invention comprises a method for the selection of a monoclonal antibody according to the invention, in which comprises providing a number of monoclonal antibodies binding to Tau pS422, determining the specific binding of said antibody to phosphorylated Tau fragment of SEQ ID NO:9, to Tau pS422, to Tau and to phosphorylated MCAK fragment of SEQ ID NO:17, and selecting an antibody with a specific binding to said phosphorylated Tau fragment and said Tau pS422 of at least 10,000-fold compared to its binding to Tau, and with a specific binding to said phosphorylated Tau fragment of at least 100-fold compared to its binding to phosphorylated MCAK fragment Ile-Gln-Lys-Gln-Lys-Arg-Arg-Ser($PO_3H_2$)-Val-Asn-Ser-Lys-Ile-Pro-Ala (SEQ ID NO:17).

The invention also comprises a method for the selection of a monoclonal antibody according to the invention, in which comprises providing a number of monoclonal antibodies binding to Tau pS422, determining the specific binding of said antibody to phosphorylated Tau fragment of SEQ ID NO:9, to Tau pS422, to Tau and to phosphorylated MCAK fragment of SEQ ID NO:17, and selecting an antibody with a specific binding to said phosphorylated Tau fragment and said Tau pS422 of at least 10,000-fold compared to its binding to Tau, and with a specific binding to said phosphorylated Tau fragment and to Tau pS422 of at least 100-fold compared to its binding to phosphorylated MCAK fragment Ile-Gln-Lys-Gln-Lys-Arg-Arg-Ser($PO_3H_2$)-Val-Asn-Ser-Lys-Ile-Pro-Ala (SEQ ID NO:17).

Antibodies according to the invention have benefits for patients in need of a Tau targeting therapy. The antibodies according to the invention have new and inventive properties causing a benefit for a patient suffering from a Tauopathy, especially from AD.

The invention further provides a method for treating a patient suffering from a Tauopathy, especially from AD, comprising administering to a patient diagnosed as having such a disease (and therefore being in need of such a therapy) an antibody binding to pS422 according to the invention. The antibody is administered preferably in a pharmaceutical composition.

A further embodiment of the invention is a method for the treatment of a patient suffering from a Tauopathy, especially from AD, which comprises administering to the patient an antibody according to the invention.

The invention further comprises the use of an antibody according to the invention for the treatment of a patient suffering from a Tauopathy, especially from AD, and for the manufacture of a pharmaceutical composition according to the invention. In addition, the invention comprises a method for the manufacture of a pharmaceutical composition according to the invention.

The invention further comprises a pharmaceutical composition comprising an antibody according to the invention, optionally together with a buffer and/or an adjuvant useful for the formulation of antibodies for pharmaceutical purposes.

The invention further provides a pharmaceutical composition comprising an antibody according to the invention in a pharmaceutically acceptable carrier. In one embodiment, the pharmaceutical composition can be included in an article of manufacture or kit.

The antibody of the present invention can be used for diagnosis of a neurological disorder such as Alzheimer's disease by detecting phosphorylated Tau polypeptide. The antibody of the present invention can be also used for the specific detection of Tau pS422 or aggregated, phosphorylated Tau.

DETAILED DESCRIPTION OF THE INVENTION

Figure 1A:
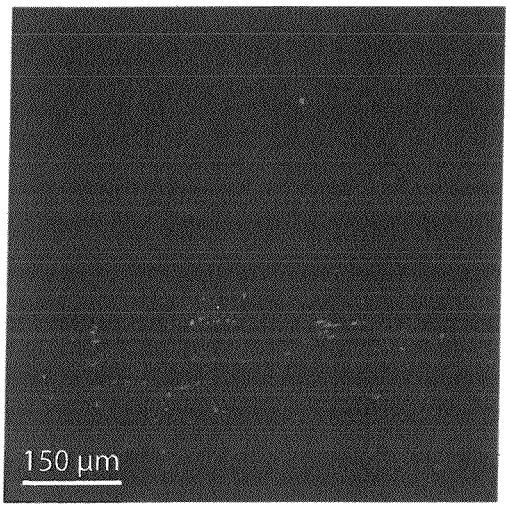
FIG. 1: Intracerebral localization of pS422 IgG1 after ip administration in the TauPS2APP mouse model. Confocal micrographs after multiple fluorescence staining with primary antibodies against IgG1 conjugated to Alexa Fluor® 488 and anti-pTau antibody AT8 conjugated to Alexa Fluor® 555 revealed bound IgG1 (A) and pTau deposits (B) together with DAPI for cell nuclei (C). Merged images show colocalized staining of anti-IgG1 and pTau in some pTau positive cells (D).
Figure 1B:
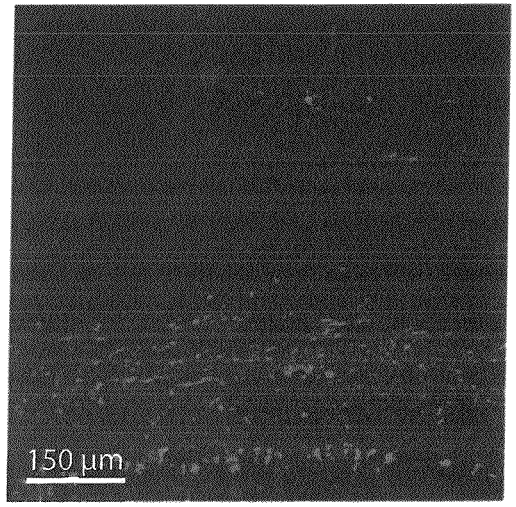
Figure 1C:
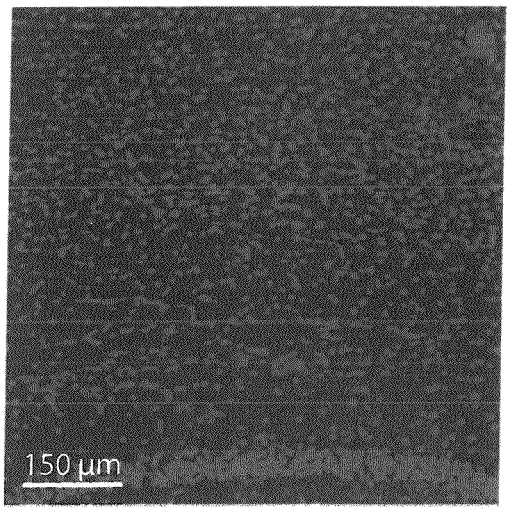
Figure 1D:
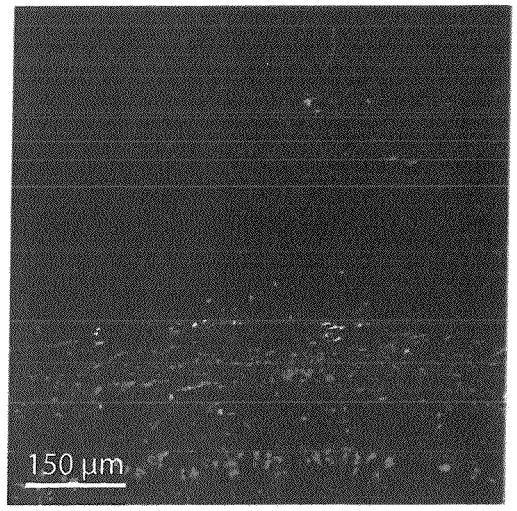
Figure 2A:
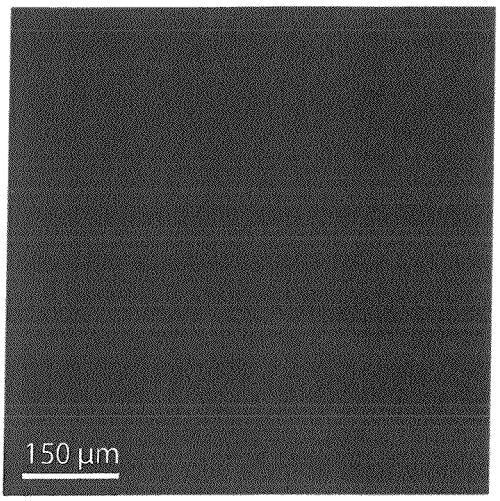
FIG. 2: Vehicle control of intracerebral localization of IgG1 in the TauPS2APP mouse model. Confocal micrographs after multiple fluorescence staining of TauPS2APP brain section showing an overview of the CA1 region of the hippocampal formation. A multiple staining with primary antibodies against IgG1 conjugated to Alexa Fluor® 488 is negative (A). Anti-pTau antibody AT8 conjugated to Alexa Fluor® 555 reveals pTau deposits (B). DAPI stain for cell nuclei (C). Merged images are shown in (D). No appreciable anti-IgG1 immunofluorescence was observed in TauPS2APP mice after injection with vehicle.
Figure 2B:
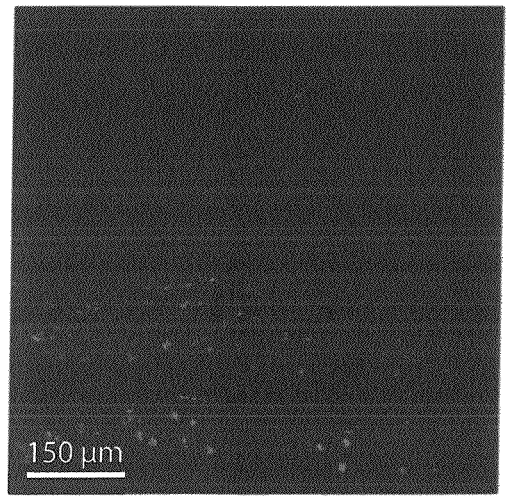
Figure 2C:
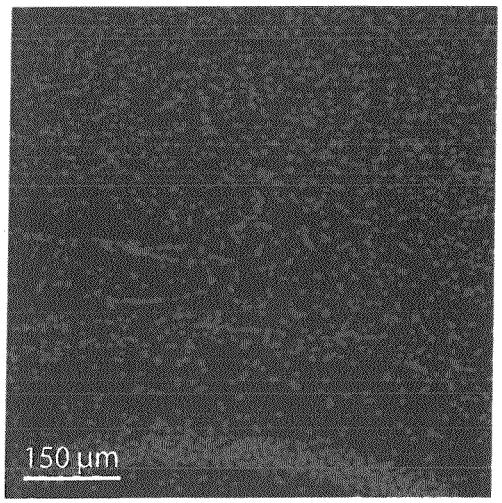
Figure 2D:
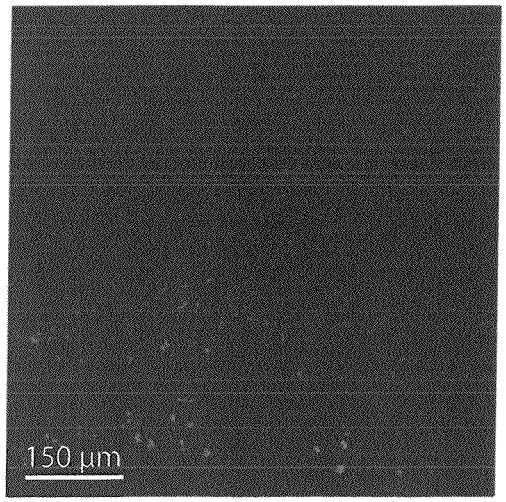

The term "Tau" according to the invention encompasses the longest isoform of human Tau, comprising 441 amino acids (isoform F, Uniprot P10636-8).

The term "phosphorylated Tau (pTau)" according to the invention encompasses the phosphorylated form of the longest isoform of human Tau, comprising 441 amino acids (isoform F, Uniprot P10636-8), generated by phosphorylation at S422 with the kinase ERK2.

The term "aggregated, phosphorylated Tau" or "aggregated (fibrillar), phosphorylated Tau" according to the invention encompasses the aggregated and phosphorylated form of the longest isoform of human Tau, comprising 441 amino acids (isoform F, Uniprot P10636-8), generated by phosphorylation of aggregated Tau with the kinase ERK2.

The term "Tau fragment" according to the invention encompasses Tau fragment Ser-Ile-Asp-Met-Val-Asp-Ser-Pro-Gln-Leu-Ala-Thr-Leu-Ala-Asp (SEQ ID NO:10)

The term "phosphorylated Tau fragment" according to the invention encompasses phosphorylated Tau fragment Ser-Ile-Asp-Met-Val-Asp-Ser(PO$_3$H$_2$)-Pro-Gln-Leu-Ala-Thr-Leu-Ala-Asp (SEQ ID NO:9).

The term "MCAK" according to the invention encompasses human mitotic centromere-associated kinesin (Kinesin-like protein KIF2C, UniProt Q99661)). MCAK_Human (88-102)[95-pSer] is a phosphorylated MCAK fragment, consisting of amino acids 88-102, phosphorylated at serine 95 (SEQ ID NO:17). This phosphorylated MCAK fragment has no sequence identity or similarity compared to phosphorylated Tau fragment of SEQ ID NO:9. The inventors recognized that antibodies according to the state of the art against phosphorylated Tau fragments may show considerable cross-reactivity with unrelated phosphorylated human peptides and proteins. For antibodies according to the invention which do not bind to phosphorylated MCAK fragment, such undesirable cross-reactivity could not be detected.

Binding to Tau pS422 and binding to Tau is investigated by ELISA with electrochemiluminescenct readout. Tau or Tau pS422 is immobilized at a concentration of 2 µg/ml and a test antibody (e.g. human or mouse) is added. For detection of bound test antibody, ruthenium-tagged anti-human or anti-mouse IgG, respectively, is added at a concentration of 0.5 µg/ml. Specific binding to Tau pS422 is found if the relation of the detection signal using Tau pS422 and Tau is at least 10,000-fold at the maximal binding signal of Tau pS422.

Binding to phosphorylated Tau fragment of SEQ ID NO:9, binding to non phosphorylated Tau fragment of SEQ ID NO:10 and to phosphorylated MCAK fragment of SEQ ID NO:17 is investigated by ELISA. A test antibody is incubated with said immobilized phosphorylated Tau fragment and for comparison with said immobilized nonphosphorylated Tau fragment or MCAK fragment. The antibody is labeled and the label is detected. Specific binding to phosphorylated Tau fragment is found if the relation of the detection signal using phosphorylated Tau fragment and nonphosphorylated Tau fragment is at least 100 at the maximal binding signal of phosphorylated Tau fragment and if the relation of the detection signal using phosphorylated Tau fragment and phosphorylated MCAK fragment is also at least 100 at the maximal binding signal of phosphorylated Tau fragment.

The term "epitope of Mab2.10.3" encompasses an epitope located within the phosphorylated Tau fragment Ser-Ile-Asp-Met-Val-Asp-Ser(PO$_3$H$_2$)-Pro-Gln-Leu-Ala-Thr-Leu-Ala-Asp (SEQ ID NO:9) which is specifically recognized by Mab2.10.3. The epitope binding property of a Tau antibody according to the present invention is determined by an in vitro crossblocking binding assay, such as the Biacore™ in vitro crossblocking binding assay, to determine the ability of Mab2.10.3 to sterically hinder the binding of the test antibody to pTau. For such an assay, Mab2.10.3 is captured as primary antibody to the Biacore™ sensor, followed by sequential injections of pTau and the secondary antibody to be tested. If the secondary antibody does not show any detectable binding signal, then the secondary antibody binds to the same epitope as Mab2.10.3.

The antibody according to the invention binds to Tau pS422 with an affinity of $5 \times 10^{-8}$ M$^{-1}$ to $10^{-12}$ M$^{-1}$ as determined by the Biacore™ analysis described above.

Binding to fibrillar aggregates of Tau pS422 is investigated by Biacore™ analysis. For this assay aggregated Tau pS422 is immobilized and the test antibody is added in different concentrations, using a dilution factor of 2, and a maximal concentration of 200 nM. An antibody according to the invention binds to fibrillar Tau pS422 with a Kd of 0.1 to 30, preferably with a Kd of 10 to 20 nM.

The term "monoclonal antibody or antibody" encompasses the various forms of an antibody, preferably a monoclonal antibody and especially preferred a IgG1 or IgG4 monoclonal antibody. The antibody according to the invention is preferably a human antibody, humanized antibody, chimeric antibody, or further genetically engineered antibody as long as the characteristic properties according to the invention are retained. T cell epitope depleted antibodies can be generated using methods described in WO 98/08097.

"Antibody fragments" comprise a portion of a full length antibody, preferably the variable domain thereof, or at least the antigen binding site thereof. Examples of antibody fragments include diabodies, single-chain antibody molecules, and multispecific antibodies fainted from antibody fragments. scFv antibodies are, e.g., described in Huston, J. S., Methods in Enzymol. 203 (1991) 46-88. In addition, antibody fragments comprise single chain polypeptides having the characteristics of a $V_H$ domain, namely being able to assemble together with a $V_L$ domain, or of a $V_L$ domain binding to Tau pS422, namely being able to assemble together with a $V_H$ domain to a functional antigen binding site.

The term "humanized antibody" refers to antibodies in which the framework and/or "complementary determining regions" (CDR) have been modified to comprise the CDR of an immunoglobulin of different species as compared to that of the parent immunoglobulin. In a preferred embodiment,
a) CDR1H of SEQ ID NO:6, CDR2H of SEQ ID NO:7, CDR3H of SEQ ID NO:8 and CDR1L of SEQ ID NO:3, CDR2L of SEQ ID NO:4, CDR3L of SEQ ID NO:5,
b) CDR1H of SEQ ID NO:23, CDR2H of SEQ ID NO:24, and CDR3H of SEQ ID NO:25, and CDR1L of SEQ ID NO:27, CDR2L of SEQ ID NO:28, CDR3L of SEQ ID NO:29,
c) CDR1H of SEQ ID NO:31, CDR2H of SEQ ID NO:32, and CDR3H of SEQ ID NO:33, and CDR1L of SEQ ID NO:35, CDR2L of SEQ ID NO:36, CDR3L of SEQ ID NO:37,
d) CDR1H of SEQ ID NO:39, CDR2H of SEQ ID NO:40, and CDR3H of SEQ ID NO:41, and CDR1L of SEQ ID NO:43, CDR2L of SEQ ID NO:44, CDR3L of SEQ ID NO:45,
e) CDR1H of SEQ ID NO:47, CDR2H of SEQ ID NO:48, and CDR3H of SEQ ID NO:49, and CDR1L of SEQ ID NO:51, CDR2L of SEQ ID NO:52, CDR3L of SEQ ID NO:53,
f) CDR1H of SEQ ID NO:55, CDR2H of SEQ ID NO:56, and CDR3H of SEQ ID NO:57, and CDR1L of SEQ ID NO:59, CDR2L of SEQ ID NO:60, CDR3L of SEQ ID NO:61, or
g) CDR1H of SEQ ID NO:63, CDR2H of SEQ ID NO:64, and CDR3H of SEQ ID NO:65, and CDR1L of SEQ ID NO:67, CDR2L of SEQ ID NO:68, CDR3L of SEQ ID NO:69
are grafted into the framework region of a human antibody to prepare the "humanized antibody". See, e.g., Riechmann, L., et al., Nature 332 (1988) 323-327; and Neuberger, M. S., et al., Nature 314 (1985) 268-270.

The "variable domain" (variable domain of a light chain ($V_L$), variable domain of a heavy chain ($V_H$)) as used herein denotes each of the pair of light and heavy chain domains which are involved directly in binding the antibody to the antigen. The variable light and heavy chain domains have the same general structure and each domain comprises four framework (FR) regions whose sequences are widely conserved, connected by three "hypervariable regions" (or complementary determining regions, CDRs). The framework regions adopt a β-sheet conformation and the CDRs may form loops connecting the β-sheet structure. The CDRs in each chain are held in their three-dimensional structure by the framework regions and form together with the CDRs from the other chain the antigen binding site. The antibody's heavy and light chain CDR3 regions play a particularly important role in the binding specificity/affinity of the antibodies according to the invention and therefore provide a further object of the invention.

The term "antigen-binding portion of an antibody" when used herein refers to the amino acid residues of an antibody which are responsible for antigen-binding. The antigen-binding portion of an antibody comprises amino acid residues from the "complementary determining regions" or "CDRs". "Framework" or "FR" regions are those variable domain regions other than the hypervariable region residues as herein defined. Therefore, the light and heavy chain variable domains of an antibody comprise from N- to C-terminus the domains FR1, CDR1, FR2, CDR2, FR3, CDR3, and FR4. Especially, CDR3 of the heavy chain is the region which contributes most to antigen binding and defines the antibody's properties. CDR and FR regions are determined according to the standard definition of Kabat et al., Sequences of Proteins of Immunological Interest, 5th ed., Public Health Service, National Institutes of Health, Bethesda, Md. (1991) and/or those residues from a "hypervariable loop".

The term "CDR1H" denotes the CDR1 region of the heavy chain variable region calculated according to Kabat. CDR2L, CDR3H, etc. mean the respective regions from the heavy (H) or light (L) chain. For example, an antibody comprising CDR1H of SEQ ID NO:6 means that the antibody comprises this amino acid sequence as a heavy chain variable chain CDR1 region in its variable heavy chain. For example, an antibody comprising CDR1H of SEQ ID NO:6, CDR2H of SEQ ID NO:7, CDR3H of SEQ ID NO:8 means that the antibody comprises in its heavy chain as sequence of CDR1 SEQ ID NO:6, as sequence of CDR2 SEQ ID NO:7, and as sequence of CDR3 SEQ ID NO:8.

The terms "nucleic acid" or "nucleic acid molecule" as used herein are intended to include DNA molecules and RNA molecules. A nucleic acid molecule can be single-stranded or double-stranded, but preferably is double-stranded DNA.

The term "amino acid" as used within this application denotes the group of naturally occurring carboxy α-amino acids comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

A nucleic acid is "operably linked" when it is placed into a functional relationship with another nucleic acid. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are colinear, and, in the case of a secretory leader, contiguous and in reading frame. However, enhancers do not have to be contiguous. Linking is accomplished by ligation at convenient restriction sites. If such sites do not exist, synthetic oligonucleotide adaptors or linkers are used in accordance with conventional practice.

As used herein, the expressions "cell", "cell line", and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included.

The "Fc part" of an antibody is not involved directly in binding of an antibody to an antigen, but exhibits various effector functions. An "Fc part of an antibody" is a term well known to the skilled artisan and defined on the basis of papain cleavage of antibodies. Depending on the amino acid sequence of the constant region of their heavy chains, antibodies or immunoglobulins are divided into the classes: IgA, IgD, IgE, IgG and IgM, and several of these can be further divided into subclasses (subtypes), e.g. IgG1, IgG2, IgG3, and IgG4, IgA1, and IgA2. According to the heavy chain constant regions the different classes of immunoglobulins are called α, δ, ε, γ, and μ, respectively. The antibody according to the invention preferably comprises an Fc part of human origin which is of IgG1 or IgG4 subtype.

Human constant light and heavy chains and IgG1 or IgG4 subtype constant chains are well known in the state of the art and e.g. described by Kabat (see e.g. Johnson, G. and Wu, T. T., Nucleic Acids Res. 28 (2000) 214-218). For example, a useful human heavy chain constant region comprises an amino acid sequence of SEQ ID NO:13 or 14 (IgG1) or of SEQ ID NO:15 or 16 (IgG4). For example, a useful human light chain constant region comprises an amino acid sequence of a kappa-light chain constant region of SEQ ID NO:11. It is further preferred that the antibody is of mouse origin and comprises the antibody variable sequence frame of a mouse antibody according to Kabat (see e.g. Sequences of Proteins of Immunological Interest, Kabat, E. A. et al., 5$^{th}$ edition, DIANE Publishing (1992)).

The invention comprises a method for the treatment of a patient in need of therapy, which comprises administering to the patient an antibody according to the invention.

The invention comprises the use of an antibody according to the invention for therapy.

The invention comprises the use of an antibody according to the invention for the preparation of a medicament for the treatment of a Tauopathy, especially AD.

The invention comprises the use of an antibody according to the invention for the treatment of brain diseases, preferably for the treatment of a Tauopathy, especially AD.

A further embodiment of the invention is a method for the production of an antibody according to the invention, which comprises inserting the sequence of a nucleic acid encoding the heavy chain of an antibody according to the invention and the nucleic acid encoding the light chain of said antibody into one or two expression vector(s), said vector(s) is/are inserted in a eukaryotic host cell, the encoded antibody is expressed and recovered from the host cell or the supernatant.

The antibodies according to the invention are preferably produced by recombinant means. Such methods are widely known in the state of the art and comprise protein expression in prokaryotic and eukaryotic cells with subsequent isolation of the antibody polypeptide and usually purification to a pharmaceutically acceptable purity. For the protein expression nucleic acids encoding light and heavy chains or fragments thereof are inserted into expression vectors by standard methods. Expression is performed in appropriate prokaryotic or eukaryotic host cells, such as CHO cells, NS0 cells, SP2/0 cells, HEK293 cells, COS cells, yeast, or E. coli cells, and the antibody is recovered from the cells (from the supernatant or after cells lysis).

Recombinant production of antibodies is for example described in the review articles of Makrides, S. C., Protein Expr. Purif. 17 (1999) 183-202; Geisse, S. et al., Protein Expr. Purif. 8 (1996) 271-282; Kaufman, R. J., Mol. Biotechnol. 16 (2000) 151-160; Werner, R. G., Drug Res. 48 (1998) 870-880.

The antibodies can be present in whole cells, in a cell lysate, or in a partially purified, or substantially pure form. Purification is performed in order to eliminate other cellular components or other contaminants, e.g., other cellular nucleic acids or proteins, by standard techniques (see Ausubel, F. et al. (eds.), Current Protocols in Molecular Biology, Greene Publishing and Wiley Interscience, New York (1987)).

Expression in NS0 cells is described by, e.g., Barnes, L. M. et al., Cytotechnology 32 (2000) 109-123; Barnes, L. M. et al., Biotech. Bioeng. 73 (2001) 261-270. Transient expression is described by, e.g., Durocher, Y. et al., Nucl. Acids. Res. 30 (2002) E9. Cloning of variable domains is described by Orlandi, R. et al., Proc. Natl. Acad. Sci. USA 86 (1989) 3833-3837; Carter, P. et al., Proc. Natl. Acad. Sci. USA 89 (1992) 4285-4289; Norderhaug, L. et al., J. Immunol. Methods 204 (1997) 77-87. A preferred transient expression system (HEK 293) is described by Schlaeger, E.-J. and Christensen, K., in Cytotechnology 30 (1999) 71-83, and by Schlaeger, E.-J., in J. Immunol. Methods 194 (1996) 191-199.

Monoclonal antibodies are suitably separated from the culture medium by conventional immunoglobulin purification procedures such as, for example, protein A-Sepharose, hydroxylapatite chromatography, gel electrophoresis, dialysis, or affinity chromatography. DNA and RNA encoding the monoclonal antibodies is readily isolated and sequenced using conventional procedures. The hybridoma cells can serve as a source of such DNA and RNA. Once isolated, the DNA can be inserted into expression vectors, which are then transfected into host cells, such as HEK 293 cells, CHO cells, or myeloma cells that do not otherwise produce immunoglobulin protein, to obtain the synthesis of recombinant monoclonal antibodies in the host cells.

Nucleic acid molecules encoding amino acid sequence variants of anti-pS422 antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of humanized anti-pS422 antibody.

The heavy and light chain variable domains according to the invention are combined with sequences of promoter, translation initiation, constant region, 3' untranslated region, polyadenylation, and transcription termination to form expression vector constructs. The heavy and light chain expression constructs can be combined into a single vector, co-transfected, serially transfected, or separately transfected into host cells which are then fused to form a single host cell expressing both chains.

In another aspect, the present invention provides a composition, e.g. a pharmaceutical composition, containing one or a combination of monoclonal antibodies, or the antigen-binding portion thereof, of the present invention, formulated together with a pharmaceutically acceptable carrier.

As used herein, "pharmaceutically acceptable carrier" includes any and all solvents, dispersion media, coatings, antibacterial and antifungal agents, isotonic and absorption/resorption delaying agents, and the like that are physiologically compatible. Preferably, the carrier is suitable for injection or infusion.

A composition of the present invention can be administered by a variety of methods known in the art. As will be appreciated by the skilled artisan, the route and/or mode of administration will vary depending upon the desired results.

Pharmaceutically acceptable carriers include sterile aqueous solutions or dispersions and sterile powders for the preparation of sterile injectable solutions or dispersion. The use of such media and agents for pharmaceutically active substances is known in the art. In addition to water, the carrier can be, for example, an isotonic buffered saline solution.

Regardless of the route of administration selected, the compounds of the present invention, which can be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention can be varied so as to obtain an amount of the active ingredient which is effective to achieve the desired therapeutic response for a particular patient, composition, and mode of administration, without being toxic to the patient (effective amount). The selected dosage level will depend upon a variety of pharmacokinetic factors including the activity of the particular compositions of the present invention employed, or the ester, salt or amide thereof, the route of administration, the time of administration, the rate of excretion of the particular compound being employed, other drugs, compounds and/or materials used in combination with the particular compositions employed, the age, sex, weight, condition, general health and prior medical history of the patient being treated, and like factors well known in the medical arts.

The invention comprises the use of the antibodies according to the invention for the treatment of a patient suffering from a Tauopathy, especially from AD.

The invention comprises also a method for the treatment of a patient suffering from such disease by administering an antibody according to the invention to the patient.

The invention further provides a method for the manufacture of a pharmaceutical composition comprising an antibody according to the invention together with a pharmaceutically acceptable carrier and the use of the antibody according to the invention for such a method.

The invention further provides the use of an antibody according to the invention for the manufacture of a pharmaceutical agent, preferably together with a pharmaceutically acceptable carrier, for the treatment of a patient suffering from a Tauopathy, especially from AD.

The invention also provides the use of an antibody according to the invention for the manufacture of a pharmaceutical agent, preferably together with a pharmaceutically acceptable carrier, for the treatment of a patient suffering from cancer, especially from a Tauopathy, especially from AD.

The following examples, sequence listing and figures are provided to aid the understanding of the present invention, the true scope of which is set forth in the appended claims. It is understood that modifications can be made in the procedures set forth without departing from the spirit of the invention.

Example 1

Preparation and Purification of Antibodies a) Antibody Generation

Mice were immunized with a Tau fragment of SEQ ID NO:9 (Ser-Ile-Asp-Met-Val-Asp-Ser(PO$_3$H$_2$)-Pro-Gln-Leu-Ala-Thr-Leu-Ala-Asp) which corresponds to amino acids 416-430 of the longest human isoform of Tau. To allow directed coupling via thiol to KLH a cysteine was added N-terminally to the Tau fragment. The subsequent immunization protocol, fusion and cloning and screening for anti-Tau pS422 specific antibodies is described in EP 1 876 185.

b) Purification of Clones 2.10.3, 2.20.4 and 5.6.11

Cell-free hybridoma culture supernatant (250-300 ml) was loaded on a 25 ml MEP Hypercell column (pall Biosciences) which was equilibrated with 50 mM TrisCl pH8.0. After washing with equilibration buffer the antibody was eluted with 30 mM sodium citrate, 100 mM NaCl pH4.1. Antibody-containing fractions were pooled and then dialyzed in Spectra-Por 6-8000 dialysis tubing overnight at 4° C. against 5 liter of 10 mM TrisCl pH8.0. The dialyzed material was loaded on a 10 ml Source 17Q column (GE Healthcare) which was equilibrated in 10 mM TrisCl pH8.0 (buffer A). After washing with buffer A the antibody was eluted with a gradient from 0-25% buffer B in 10 column volumes. Buffer B contained 10 mM TrisCl, 1M NaCl pH8.0. The antibody eluted at about 200 mM NaCl. The purity of the individual fractions was checked by SDS-PAGE and the purest fractions pooled.

One day prior to injection into mice, each antibody was dialyzed against PBS and the antibody concentration adjusted to 3.2 mg/ml.

Example 2

Preparation of Tau, Tau pS422, Aggregated Tau and Aggregated Tau pS422

Tau containing an N-terminal (His)$_6$-SUMO fusion tag was expressed in *E. coli* and purified by ion-exchange chromatography on HiTrapQ (GE Healthcare, Switzerland) followed by affinity chromatography on Ni-NTA Sepharose (Qiagen, Switzerland). The fusion tag was subsequently cleaved by digestion with SUMO protease (Invitrogen, Netherlands) followed by a second Ni-NTA Sepharose chromatography step to remove the fusion tag.

Tau-pSer422 was prepared by incubation of Tau with ERK2 protein kinase. The molar ratio of ERK2:Tau (ca:1:10) was chosen to yield maximal phosphorylation at S422 following overnight incubation at 37° C. in 10 mM TrisCl pH8.0 containing 1 mM MgCl$_2$ and 2 mM ATP. It was then assumed that this represents stoichiometric phosphorylation at the 422 site. Phosphorylation was checked by western blot using an in-house monoclonal antibody specific for pS422 in Tau.

Figure 10:
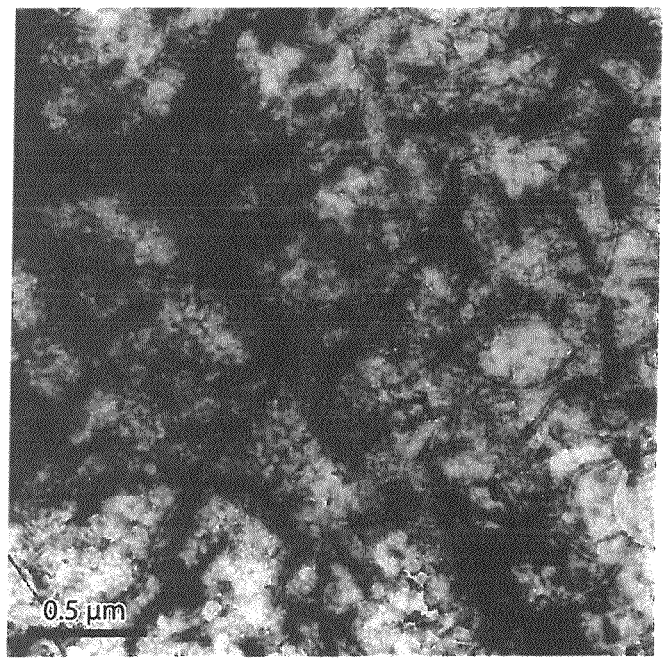
FIG. 10: In vitro aggregated Tau is fibrillar. Electron micrograph of negatively-stained aggregated Tau.
Figure 11:
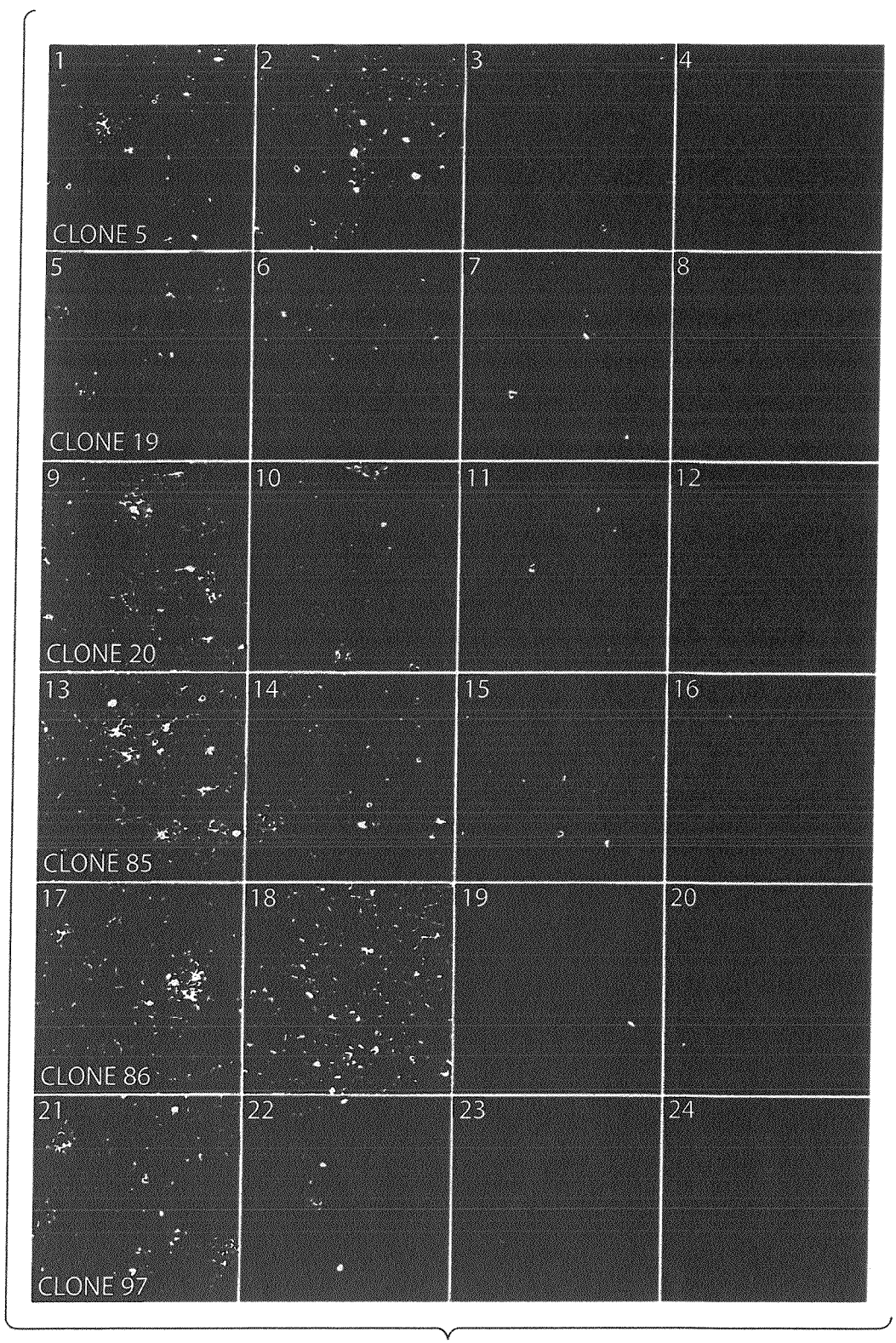
FIG. 11: Fluorescent micrographs of human cortical AD brain sections stained with anti-Tau pS422 rabbit monoclonal antibodies Mab 005 (first row), Mab 019 (second row), Mab 020 (third row), Mab 085 fourth row), Mab 086 8fifth row) and Mab 097 (sixth row)) showing positive labelled pTau deposits and filaments. Serial dilution of IgGs are shown in each row starting with 2.0 µg/ml (left), 0.4 µg/ml, 0.08 µg/ml and 0.016 µg/ml.

Aggregated (fibrillar) Tau was prepared by incubating purified Tau at a final concentration of 5 μM in 10 mM TrisCl pH8.0 containing 50 μM arachidonic acid (Sigma, Switzerland). The incubation was carried out at 37° C. for 16 h. Aggregation status was checked by fluorescence spectroscopy in the presence of 10 μM Thio S (Barghorn and Mandelkow [2002] Biochemistry 41:14885-14896) and by electron microscopy (FIG. 10). As FIG. 10 shows, aggregated Tau has a fibrillar appearance. Aggregated, phosphorylated Tau was prepared by incubating pre-aggregated Tau with ERK2 kinase as described above.

Example 3

Anti-Tau pS422 Monoclonal Antibodies are Highly Selective for Tau Phosphorylated at S422 a) Peptide Synthesis

Peptide syntheses were performed in an automated peptide synthesizer using Fmoc chemistry. In iterative cycles the peptide sequences were assembled by sequential coupling of the corresponding Fmoc-amino acids. In every coupling step, the N-terminal Fmoc-group was removed by treatment of the resin with 20% piperidine in N-methylpyrrolidone. Couplings were carried out employing Fmoc-protected amino acids (1 mmol) activated by HBTU/HOBt (1 mmol each,) and DIPEA (2 mmol) in DMF. After every coupling step, unreacted amino groups were capped by treatment with a mixture of acetic acid (0.5 M), DIPEA (0.125 M) and HOBt (0.015 M) in NMP (10 min vortex). Between each step, the resin was washed with N-methylpyrrolidone and DMF. Incorporation of sterically hindered amino acids was accomplished in automated double couplings. For this purpose, the resin was treated twice with 1 mmol of the activated building block without a capping step in between coupling cycles. In the phosphorylated peptide sequences the corresponding serine derivative was incorporated as Fmoc-Ser(PO(OBzl)OH)—OH building block. Upon completion of the target sequences, Fmoc-Glu(biotinyl-PEG)-OH (Biotin attached via a PEG-spacer) was coupled to the MCAK peptide using standard amino acid coupling conditions, whereas 4×β-alanine (U) and 1×ε-lysine was attached to the phospho-Tau sequences employing standard conditions. Subsequently, DMTr-biotin was conjugated to the phospho-Tau peptides yielding the biotinylated target sequences. After final Fmoc deprotection (for MCAK only), all peptide resins were placed separately into filter frits and treated with a mixture of trifluoroacetic acid, water and triisopropylsilane (19 mL:0.5 mL:0.5 mL) for 2.5 h. The cleavage solutions were filtered and the peptides were precipitated by addition of cold (0° C.) diisopropyl ether (300 mL) to furnish colorless solids, which were repeatedly washed with diisopropyl ether. The crude products were re-dissolved in a mixture of acetic acid/water, lyophilized and subsequently purified by preparative reversed phase HPLC employing an acetonitrile/water gradient containing 0.1% TFA.

HBTU: 2-(1H-benzotriazole-1-yL)-1,1,3,3-tetramethyluro-niumhexafluorophosphate
HOBt: Hydroxybenzotriazole
DIPEA: N,N-Diisopropylethylamine
NMP: N-methyl-2-pyrrolidone b) Assay with Phosphorylated Tau Peptide Peptides representing the Tau pS422 sequence 416-430 (phosphorylated and non phosphorylated) and MCAK_Human (88-102)[95-pSer] were synthesized and biotinylated to allow the coating to a streptavidin labeled microtiter plate. To test for maximal binding of Tau phosphopeptide to the assay plates, different concentrations of Tau phosphopeptide ranging from 1 ng/ml to 2000 ng/ml were used for coating. Finally 50 ng/ml Tau phosphopeptide was used for coating for 60 min at room temperature. Anti Tau pS422 antibodies 2.10.3., 2.20.4. and 5.6.11 were incubated in the peptide labeled microtiter plates for 60 min in concentrations up to 1000 ng/ml. After washing, the binding of the antibodies was detected using an anti-mouse-IgG Fc antibody which was POD-labeled. After incubation with ABTS® for 20 min at room temperature absorbance (O.D.) at 405 nm-492 nm was measured. The antibody binding was determined by $EC_{50}$. Typical $EC_{50}$ value could be determined in the range of 100 ng/ml for 2.10.3., 8 ng/ml for 2.20.4. and 1 ng/ml for 5.6.11. The nonphosphorylated Tau fragment and (MCAK_Human (88-102)[95-pSer]) were used as controls. No binding of the control peptides could be observed. Typical back-ground values were around 30 mE (Table 1), which is about 1% of the maximal value measured with phosphorylated Tau fragment. Therefore Mab2.10.3 binds to phosphorylated Tau fragment with a selectivity of at least 100-fold compared to nonphosphorylated Tau peptide of SEQ ID NO:10 and to MCAK_Human (88-102)[95-pSer]. Results are shown in Table 1.

TABLE 1

| Antibody | Max. O.D. phosphorylated Tau fragment binding | Max O.D. Tau fragment binding | Relation (O.D. phosphorylated Tau fragment/ O.D. Tau fragment) | O.D. phosphorylated MCAK fragment |
|---|---|---|---|---|
| 2.10.3. | 3300 mE | 30 mE | 110 | 30 mE | c) Assay with Full-Length Tau and Tau pS422

Assays were performed using the Meso Scale Discovery® assay platform (MSD, Gaithersburg, Md., USAMD). MSD 96-well microtitre plates were coated with Tau or Tau pS422 at a concentration of 2 μg/ml in PBS buffer for 1 h at room temperature. Plates were then blocked by adding PBS containing 5% BSA and 1% Tween 20 for 1 h. Antibodies were diluted in Low Cross Buffer (MSD) containing 0.1% BSA and 0.1% Tween®20 at a concentration of 30 pg/ml to 20 ng/ml (except for clone 2.10.3 where the concentration range was 3 ng/ml to 250 ng/ml) and added to the coated, blocked plates and incubated for 3 h at room temperature. The plates were then washed three times with PBS buffer containing 1% Tween. For detection of bound antibody, SULFO-tagged anti-mouse IgG (MSD) was added at a concentration of 0.5 μg/ml and the plates incubated for 1 h at room temperature. After addition of Read Buffer (MSD), plates were read in a MSD Sector Imager 6000 plate reader. FIG. 9 A-D shows the data obtained using either Tau or Tau pS422 as binding partner for the anti-Tau pS422 monoclonal antibodies (clone 5.6.11 (FIG. 9B), 2.20.3 (FIG. 9C) and 2.10.4 (FIG. 9D)). The Tau pS422 antibodies are compared for reference with an anti-Tau antibody (clone 4/2) (FIG. 9A) that recognizes both Tau and Tau pS422. By comparing binding to Tau pS422 and Tau, it was found that signals for binding to Tau were not distinguishable from background signals and therefore no binding to Tau was detected. Therefore it was calculated that each of the three anti-Tau pS422 antibodies binds to Tau pS422 with a selectivity of at least 10,000-fold compared to Tau.

Example 4

Anti-Tau pS422 Antibody Binds to Fibrillar Aggregates of Tau pS422

Biacore™ analysis was used to measure the binding of Anti-Tau pS422 (clone 2.10.3) to preparations of aggregated, fibrillar Tau pS422. The phosphorylated fibrils are considered to be an in vitro representation of the PHF form of Tau that occurs in Alzheimer's Disease brain. Fibrillar material was prepared and phosphorylated as described in Example 2.

Immobilization on Sensor Chips:

Aggregated Tau pS422 was immobilized covalently by amine coupling on a CM5-sensor chip. For that purpose, aggregated Tau pS422 was diluted 19 fold in 10 mM sodium acetate pH 5.0. The activated sensor surface was contacted with the protein solution until the desired level of protein was immobilized on the chip. Afterwards the remaining reactive N-hydroxysuccinimide-esters were blocked by injecting 1 M Ethanolamine pH 8.0. 450 response units (RU) of protein was immobilized in order to characterize the binding behavior of anti-Tau pS422 (clone 2.10.3). The immobilization assay was carried out at RT and with PBS used as running buffer.

Kinetic Titration:

For the characterization of the antibody, the running buffer was changed to 10 mM Tris-Cl pH 8.0, 250 mM NaCl and a concentration series of the antibody was prepared: 5 different concentrations, dilution factor 2, max. conc. 200 nM. The different solutions of antibody were injected consecutively starting with the lowest concentration. The sensor surface was regenerated with 100 mM $H_3PO_4$ after the so called kinetic titration. The measurements were carried out three times.

Data evaluations was performed by using Biaeval software. The calculation of the parameters are based on the assumption that the binding of the antibody aggregated Tau pS422 is fully monovalent. The kinetic and thermodynamic parameters characterizing the binding behavior of the antibody to the immobilized protein are shown in Table 2.

TABLE 2

| $K_D$ nM | $k_d$ $s^{-1}$ | $K_a$ M × s | $R_{max}$ RU |
|---|---|---|---|
| 17.0 | $1 \times 10^{-2}$ | $6.2 \times 10^5$ | 208 |

Thus anti-Tau pS422 (clone 2.10.3) binds to fibrillar phosphoTau with a $K_D$ of 17 nM.

Example 5

In Vitro Binding of Anti-Tau pS422 Monoclonal Antibodies to Intracellular pTau in Brain Sections from Alzheimer's Disease Patient The specific and sensitive immunodecoration of pathologically relevant pTau pathology in Alzheimer's disease brain tissue was investigated by immunohistochemical staining experiments using cryosections of human brain tissue from AD patients. Assessment was done by using frozen postmortem brain tissue from AD patients staged neuropathologically as Braak VI. Brain tissue was cryosectioned and processed for immunohistochemistry without any chemical i.e. aldehyde fixation. Detection of pTau deposits was done using a fluorescently labelled secondary antibody specific for mouse IgG and monitored by fluorescence light microscopy.

Briefly, cryostat sections of unfixed brain tissue from cortical brain regions obtained postmortem from patients that were positively diagnosed for Alzheimer's disease were labeled by indirect immunofluorescence. In the present report images obtained from orbital frontal gyms tissue from an AD patient (Case 01-05; internal brain bank) are shown. A successive two-step incubation was used to detect bound murine antibodies from different clones which are revealed by affinity-purified goat anti-mouse IgG (H+L) conjugated to Cy3 (Jackson Immuno Research). Sectioning, staining and fluorescence microscopy was done according to standard procedures.

Figure 8:
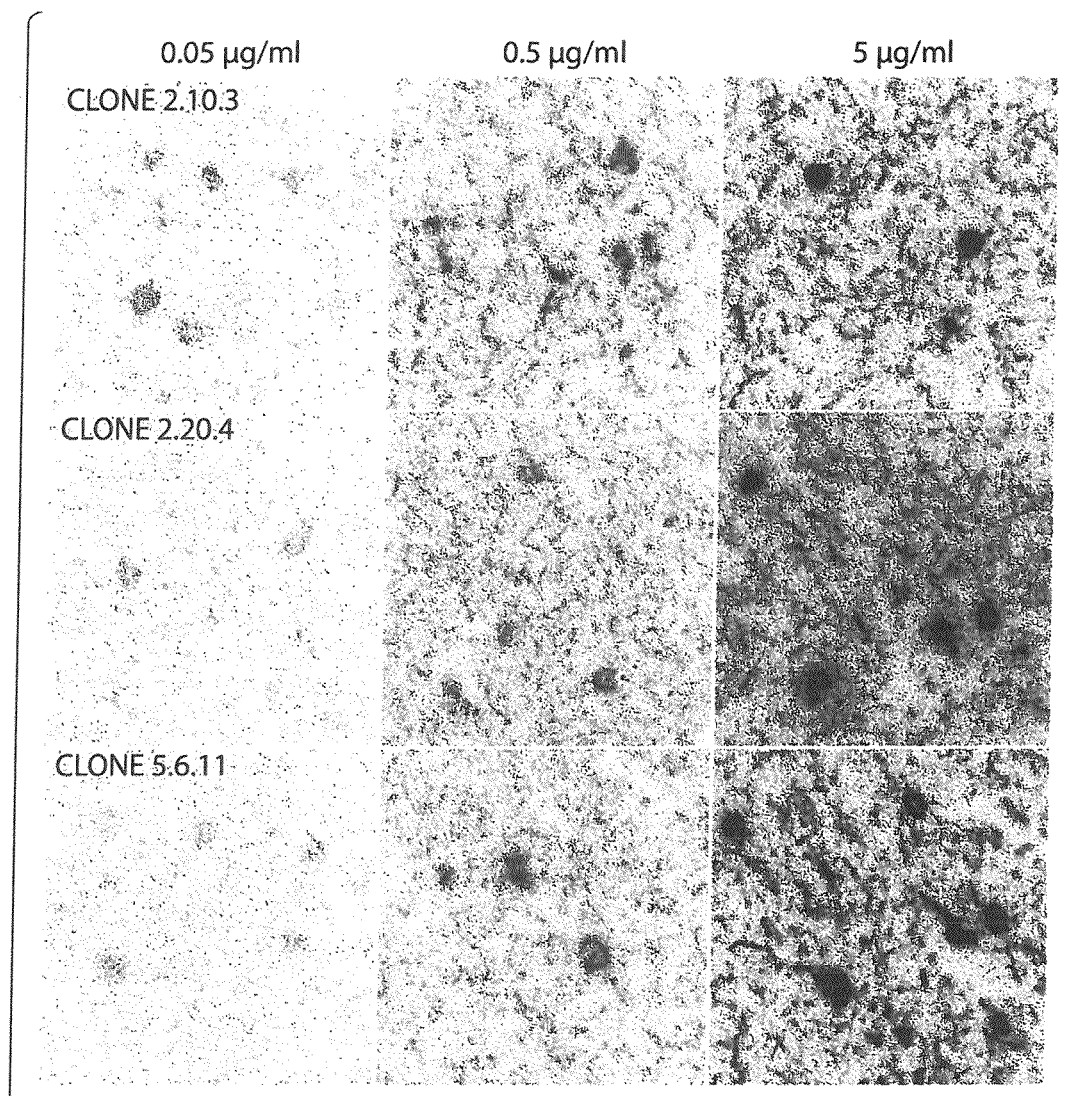
FIG. 8: In vitro binding of anti-Tau pS422 antibodies to AD brain sections. Fluorescent micrographs after staining of human cortical AD brain sections with anti-Tau pS422 monoclonal antibodies (clones 2.10.3, 2.20.4 and 5.6.11) at indicated concentration showing positive labeled pTau deposits. Intracellular pTau deposits, like large neurofibrillary tangles and elongated neuropil threads, are notable
Figure 9A:
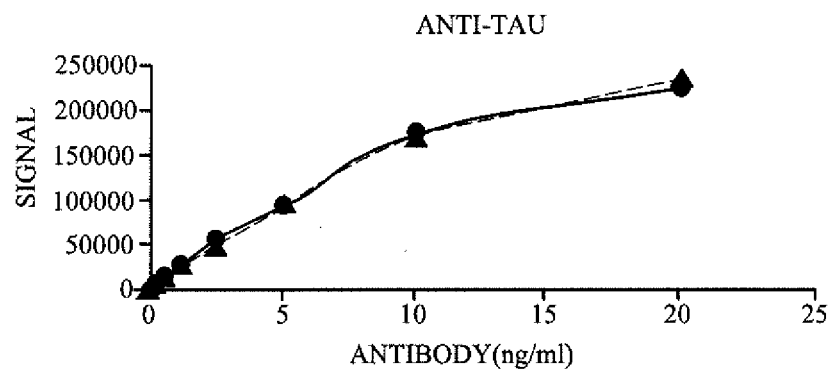
FIG. 9: Selectivity of anti-Tau pS422 compared to Tau pS422 compared to Tau. Measurement by ELISA of selectivity of anti-Tau pS422 antibodies using Tau (▲) or Tau pS422 (•) coated plates. Clone 5.6.11 (FIG. 9B) is compared to Anti-Tau (FIG. 9A) measurements and clone 2.10.03 (FIG. 9C) and clone 2.204 (FIG. 9D).
Figure 9B:
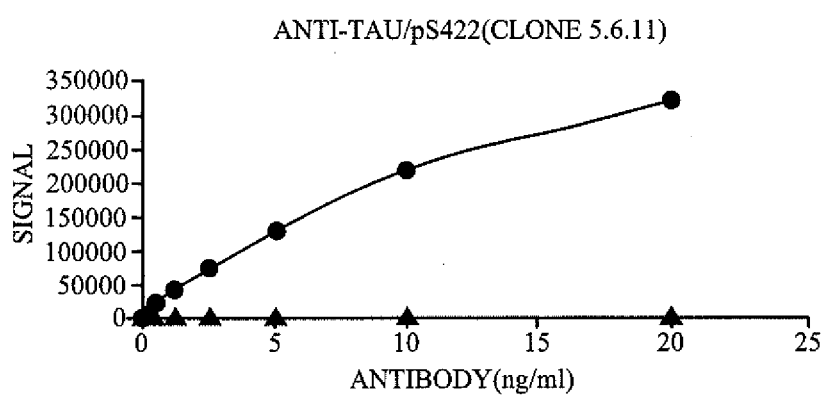
Figure 9C:
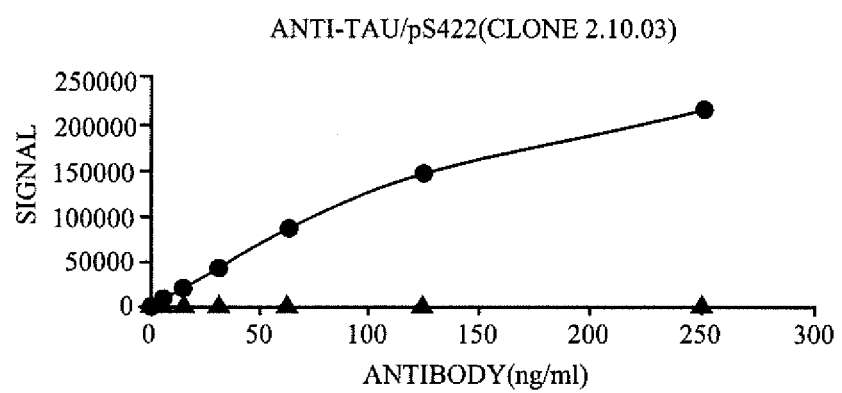
Figure 9D:
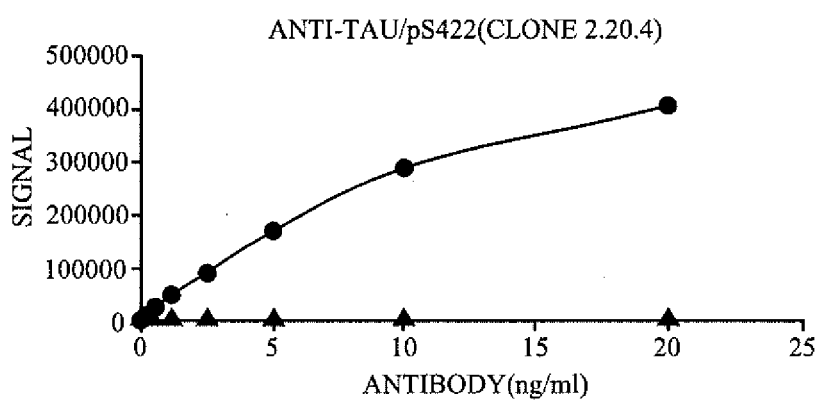

Specific and sensitive staining of pTau pathology is evident for clones 2.10.3, 2.20.4 and 5.6.11 (FIG. 8). A consistent staining of all types of pTau deposits, namely neurofibrillary tangles, neuropil threads and dystrophic neurites is clearly visible. A minimal effective concentration of 0.05 µg/ml was determined for all investigated clones, which indicates highly sensitive binding to genuine human pTau deposits.

Detection of pTau deposits can also be done by using an IgG4 antibody according to the invention and a fluorescently labelled secondary antibody specific for human IgG4 and monitored by fluorescence light microscopy.

Example 6

Generation of TauPS2APP Triple Transgenic Mice

Transgenic TauPS2APP mice were generated by crossing homozygous PS2APP females from line B6.172H (Ozmen, L. et al., Neurodegen. Dis. 6 (2009) 29-36) with homozygous Tau males from line TauP301L (Goetz et al., Science 293 (2001) 1491-1495). The resulting transgenic mice are all heterozygous for human APP Swedish mutant, human Presenilin 2 N141I mutant and human Tau P301L mutant. The expression of the transgenes is driven by the murine Thy-1 promoter in case of human APP and Tau transgenes and by the prion promoter in case of human Presenilin 2 transgene.

Animals were housed with a 12-hour light-dark cycle and food and water were provided ad libitum. Housing facilities are accredited by the Accreditation of Laboratory Animal Care. All procedures were conducted in strict adherence to the Swiss federal regulations on animal protection and to the rules of the Association for Assessment and Accreditation of Laboratory Animal Care and with the explicit approval of the local veterinary authority.

Processing of mice for immunohistochemical analysis: Mice were anaesthetized using 4% isoflurane and killed by decapitation. Blood was collected in EDTANaF coated tubes (Milian). Brains were removed, frozen immediately on dry ice and stored at −80° C. until further use.

Males and females mice aged 20 months old were used in the experiments. At that age, enhanced intracellular hyperphosphorylated Tau accumulation and neurofibrillary pathology is evident in brains from all mice tested so far.

Example 7

Histology and Ultrastructural Analysis of pTau Deposits in the TauPS2APP Mouse Model The TauPS2APP mouse develops an age-dependent and progressive phenotype with intraneuronal pTau deposits with structures similar to neurofibrillary tangles detectable in several brain regions. Substantial pTau pathology is observed at 24 months of age. Typically several neurons that are positive for intracellular Tau pS422 are found within the prefrontal cortex and pyramidal cell layer of the hippocampal CA1 region and adjacent in the subiculum. It was found that at this age pTau spreads into the stratum oriens and along the hippocampal alveus border into the CA3 and fimbria region and also into the stria.

Figure 7A:
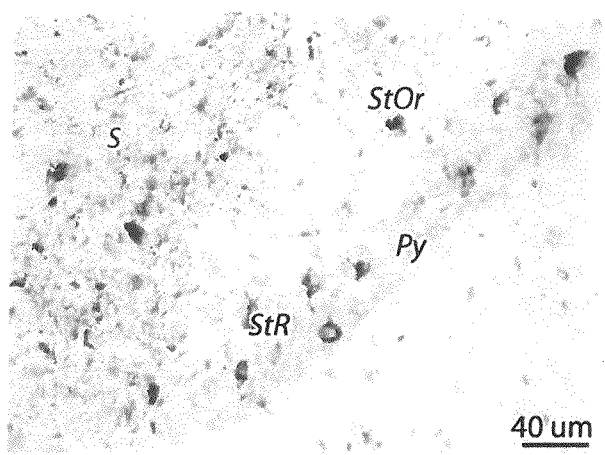
FIG. 7: Analysis of TauPS2APP mouse. A: Gallyas silver staining of a sagittal brain section of 16 month old TauPS2APP mouse. Typical tangle-like intraneuronal structures are visible in black and confirm pTau positive neurons revealed by immunofluorescence microscopy. B: Immunogold labeled ultrathin section of a 16 month old TauPS2APP mouse. Anti-Tau pS422 mAb binds specifically to fibrillar structures at a dendritic process in the hippocampal CA1 region, as revealed by the secondary antibody conjugated to 10 nm colloidal gold (arrow). Size and density of labeled fibrils suggest that they are comparable to paired helical filaments of phosphorylated Tau proteins found in degenerating neurons of Alzheimer's Disease.

Gallyas silver staining was done as described (Gallyas, F., Acta Morphologica Acad. Sci. Hung. 19 (1971) 1-8) with minor modifications, namely preincubation in 3% periodic acid and after the washing in 0.5% acetic acid an additional wash in 5% sodiumthiosulfate for 2 min. Counterstaining was done with standard hematoxilin & eosin. Gallyas silver staining confirmed the occurrence of numerous tangle-like deposits in the hippocampus and cortex of TauPS2APP mice (FIG. 7A).

The ultrastructure of pTau deposits was investigated by immuno-electron microscopy. A 16 month old TauPS2APP mice were perfused with 2% formaldehyde and 0.5% glutaraldehyde in PBS. Brain slices were embedded into Lowicryl HM20 and ultrathin sections prepared as described previously (Richards, J. G. et al., J. Neurosci. 23 (2003) 8989-9003). Briefly, sections were incubated with anti-Tau pS422 at 10 µg/ml in PBS with 2% BSA for 1 h. After 6 washes in PBS/2% BSA, the sections were incubated with a secondary goat anti-mouse IgG (Amersham, Arlington Heights, Ill.), conjugated to 10 nm gold at 1:20 in PBS/2% BSA/0.1% Tween®20 for 1 h and washed in PBS with 2% BSA. For controls, we used sections treated with normal mouse serum, which resulted in a negligible background of less than 10 gold particles in an area of 10 µm². Electron micrographs were taken with a JEOL 1210 at 100 kV.

Figure 7B:
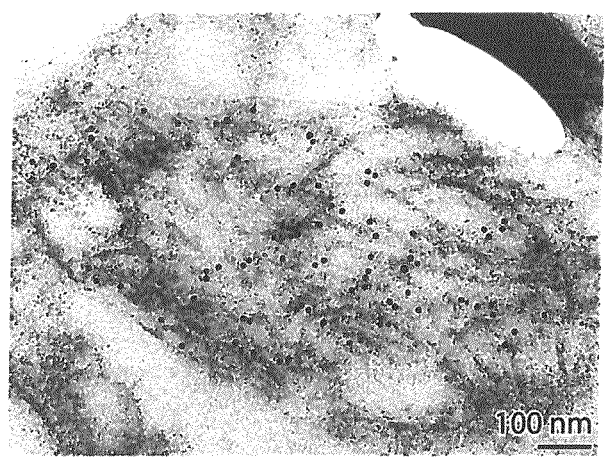

An ultrastructural examination of the hippocampus of a 16 month old TauPS2APP mice with numerous pTau positive neurons revealed immunogold labeled fibrillar deposits typical for paired helical filaments (PHF) within dendritic processes (FIG. 7B). Ultrathin sections labeled with anti-Tau pS422 mAb revealed specific binding to fibrillar structures within dendritic processes in the hippocampal CA1 region as revealed by the secondary antibody conjugated to 10 nm colloidal gold, visible as black dots (FIG. 7B). Immuno-gold labeling demonstrates that the pS422 epitope of Tau is localized to intracellular fibrillar structures in neurons of the investigated TauPS2APP mice. Size and density of labeled fibrils suggest that they are structurally comparable to the PHFs observed in degenerating neurons of patients with AD. The localization of pTau PHF clearly demonstrates the intracellular distribution of aggregated pTau deposits in transgenic TauPS2APP mice.

Example 8

In Vivo Binding of Anti-Tau pS422 Monoclonal Antibodies to Intracellular pTau in the Brains of a pTau Mouse Model of Alzheimer's Disease Revealed by Immunohistochemistry and Confocal Laser Scanning Microscopy Selected anti-Tau pS422 antibodies (see Table 1) were tested in 24 month old TauPS2APP triple transgenic mice and assessed for binding to pTau deposits in vivo. The studies were performed in the TauPS2APP mouse model that develops an age-dependent and progressive phenotype with intraneuronal pTau deposits including structures similar to neurofibrillary tangles detectable in several brain regions, as described in Example 4.

The used antibodies against Tau pS422 were administered i.p. at a dose of 20 mg/kg. Immunohistochemical stainings were done two days after ip administration to detect pTau deposits and bound mouse IgG subtype antibodies. Groups of each three mice were sacrificed two days after dosing. The mice were deeply anaesthetized (~2 minutes in 5% v/v Forene™, until the asphyxia state is almost reached), then the thorax was opened and the pericardium removed and perfused with PBS and decapitated, brains were halved and snap frozen in dry ice. Parasagittal cryostat sections of fresh-frozen brains were cut at 20 μm thickness with a cryostat (CM3050S, Leica), mounted on precooled Histobond slides (Marienfeld, Lauda-Königshofen, Germany) and stored at −20° C.

A triple immuno-fluorescence staining was applied to detect bound anti-Tau pS422 antibodies. Sections were hydrated in PBS and treated with 100% acetone precooled to −20° C. for 2 min. All further steps were done sequentially in a staining automat (Autostainer Plus DakoCytomation, High Wycombe, UK) at room temperature. Slides with brain sections were washed with PBS containing 0.01% Tween 20, pH 7.4 for 5 minutes and blocking of unspecific binding sites by sequential incubation in PBS with 1% bovine serum albumin, 1% ovalbumin and 1% normal goat serum for 20 minutes. After washing with PBS and 0.01% Tween 20, slides were incubated with IgG isotype specific detection antibodies, i.e. affinity-purified goat anti-mouse IgG1, IgG2a or IgG2b covalently conjugated to Alexa Fluor® 488 dye (A21121, A21131 or A21141, Molecular Probes) at 20 ug/ml in 1% BSA in PBS, pH 7.4 for 1 hour. After washing in PBS with 0.01% Tween 20, localization of pTau was assessed by a labeling with 5 ug/ml anti-pTau antibody (AT-8, Pierce Biotechnology), a murine monoclonal antibody for phosphorylated S202/205 epitope in Tau protein that was covalently conjugated to Alexa Fluor® 555 dye and applied in PBS with 1% bovine serum albumin, 1% ovalbumin and 1% normal goat serum for 1 hour. After washing with PBS with 0.01% Tween 20, cell nuclei were counterstained with 4,6'-diamidino-2-phenylindole (DAPI) at 1 ug/ml in PBS for 5 minutes. After washing in PBS with 0.01% Tween®20, autofluorescence of lipofuscin was reduced by quenching through incubation in 4 mM CuSO4 in 50 mM ammonium acetate, pH 5 for 30 minutes. After rinsing the slides with double-distilled water and final washing with PBS and 0.01% Tween®20, slides were embedded with fluorescence mounting medium (S3023 DakoCytomation, High Wycombe, UK). Maximum projection images were recorded sequentially at non-overlapping emission channels recorded with a Leica SP2, AOBS confocal laser scanning microscope at a pinhole setting of 1 Airy.

Substantial pTau pathology is noted in TauPS2APP mice at 24 months. Typically, several neurons that are strongly positive for intracellular Tau pS422 were found within the prefrontal cortex and pyramidal cell layer of the hippocampal CA1 region and adjacent into the subiculum. At this age, pTau was found to spread into the stratum oriens and along the hippocampal alveus border into the CA3 and fimbria region and also into the stria terminalis.

Figure 3A:
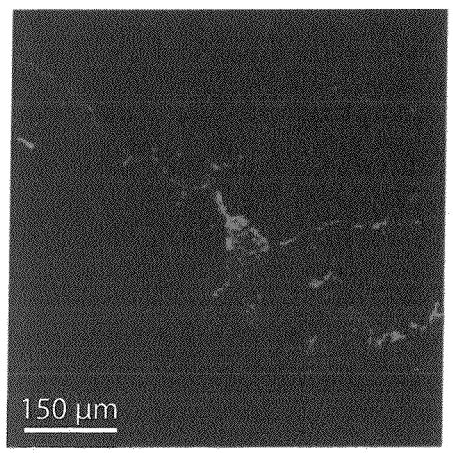
FIG. 3: Intracellular localization of IgG1 after ip administration in the TauPS2APP mouse model. Confocal micrographs after multiple fluorescence staining of TauPS2APP brain section showing a positive labeled cell within the prefrontal cortex. A multiple staining with primary antibodies against IgG1 conjugated to Alexa Fluor® 488 and anti-pTau antibody AT8 conjugated to Alexa Fluor® 555 revealed bound IgG1 (A) and pTau deposits (B). Merged images show the colocalized perinuclear and dendritic staining of anti-IgG1 and pTau together with DAPI stain for cell nuclei in blue (C).
Figure 3B:
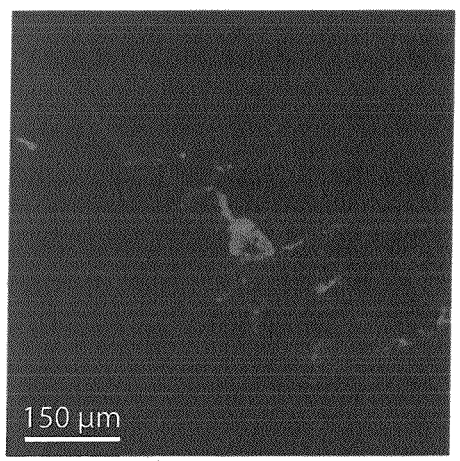
Figure 3C:
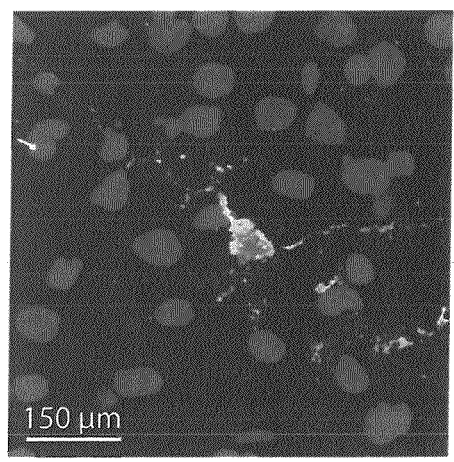
Figure 4A:
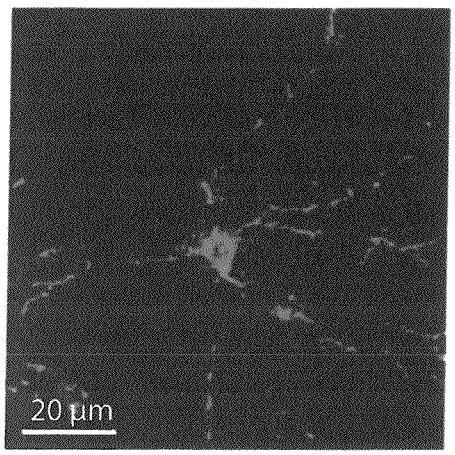
FIG. 4: Intracellular localization of IgG1 after ip administration in the TauPS2APP mouse model. Confocal micrographs after multiple fluorescence staining of TauPS2APP brain section showing a positive labeled cell within the pyramidal layer of the hippocampal CA1 region. A multiple staining with primary antibodies against IgG1 conjugated to Alexa Fluor® 488 and anti-pTau antibody AT8 conjugated to Alexa Fluor® 555 revealed bound IgG1 (A) and pTau deposits (B). Merged images show the colocalized perinuclear and dendritic staining of anti-IgG1 and pTau together with a DAPI stain for cell nuclei (C).
Figure 4B:
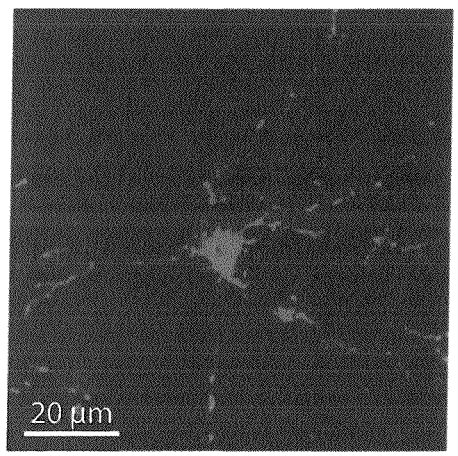
Figure 4C:
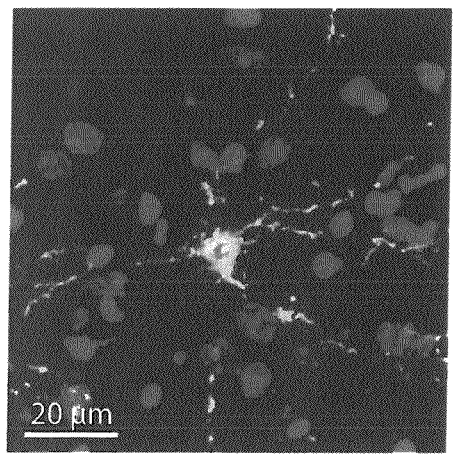
Figure 5A:
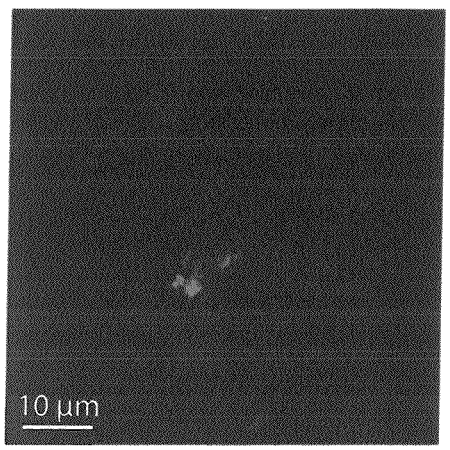
FIG. 5: Intracellular localization of IgG2a after ip administration in the TauPS2APP mouse model. Confocal micrographs after multiple fluorescence staining of TauPS2APP brain section showing positive labeled cell within the pyramidal layer of the hippocampal CA1 region. A multiple staining with primary antibodies against IgG2a conjugated to Alexa Fluor® 488 and anti-pTau antibody AT8 conjugated to Alexa Fluor® 555 revealed bound IgG2a (A) and pTau deposits (B). Merged images show the colocalized perinuclear staining of anti-IgG2a and pTau together with DAPI stain for cell nuclei (C).
Figure 5B:
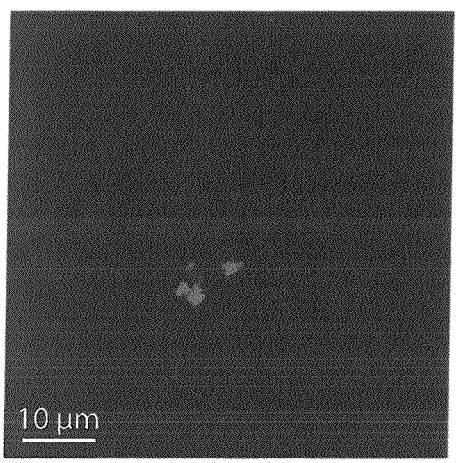
Figure 5C:
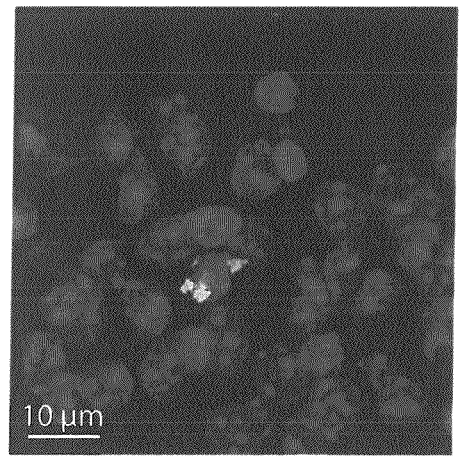
Figure 6A:
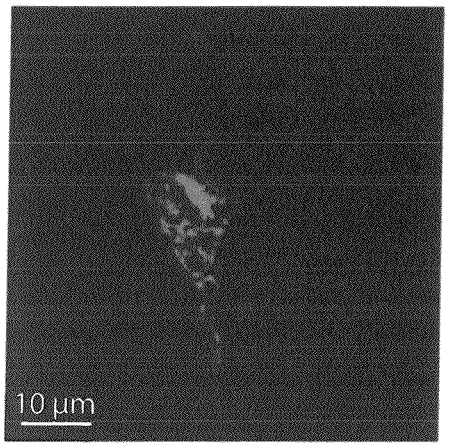
FIG. 6: Intracellular localization of IgG2b after ip administration in the TauPS2APP mouse model. Confocal micrographs after multiple fluorescence staining of TauPS2APP brain section showing positive labeled cell within the prefrontal cortex region. A multiple staining with primary antibodies against IgG2b conjugated to Alexa Fluor® 488 and anti-pTau antibody AT8 conjugated to Alexa Fluor® 555 revealed bound IgG2b (A) and pTau deposits (B). Merged images show the colocalized perinuclear staining of anti-IgG2b and pTau, indicated by the arrows (C).
Figure 6B:
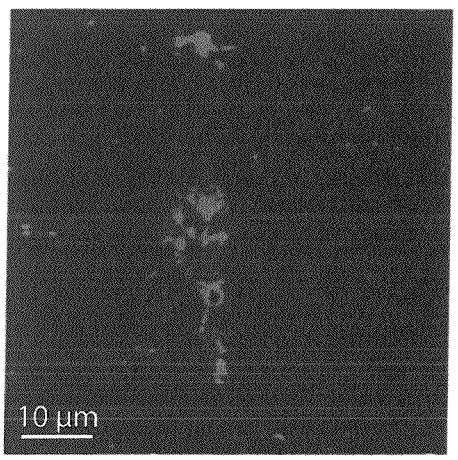
Figure 6C:
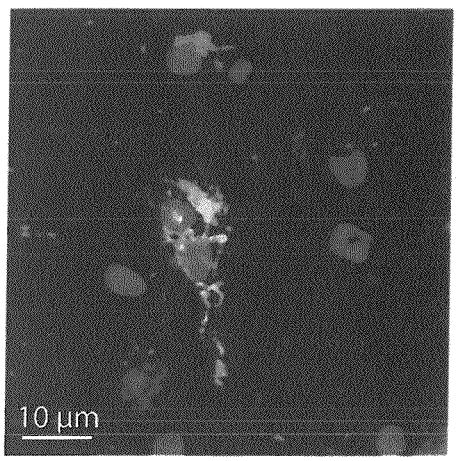

Immunostainings at the prefrontal cortical and CA1 region from the hippocampal formation of 24 month old TauPS2APP mouse are shown in confocal microscopy images (FIGS. 1-6). Clearly, intracellular pTau and administered IgG subtype antibodies were detectable and found colocalized at cells in the brain regions with substantial pTau pathology. Representative examples for intracellular IgG1 localization is shown in FIGS. 1, 3 and 4 with vehicle control (FIG. 2). IgG2a positive cells (FIG. 5) and IgG2b (FIG. 6) were also found in some cells. Some of the pTau positive cells exhibited a typical neurofibrillary morphology which is reminiscent of neurofibrillary tangles found in degenerating neurons of brain tissue from patients with AD. Colocalized immunoreactivity of mouse IgG subtype antibodies, especially for IgG1 and pTau, was observed in dendritic processes, typically in the prefrontal cortex and granular cell layer at the CA1 region of the hippocampal formation (FIGS. 3 and 4).

All tested anti-Tau pS422 antibodies showed specific binding to intracellular pTau deposits. However, the extent of binding varied between the three IgG isotypes, as shown in Table 3.

TABLE 3

| Antibody | IgG isotype | Staining intensity in TauPS2APP mouse brain |
|---|---|---|
| Tau_2.10.3 | IgG1 | XXX |
| Tau_2.20.4 | IgG2a | X |
| Tau_5.6.11 | IgG2b | X |

Where X = mild, XX = moderate and XXX = strong IHC reactivity

Example 9

Chronic Treatment with Anti-Tau pS422 Monoclonal Antibody Reduces Tau Pathology in a Mouse Model of Alzheimer's Disease The ability of murine anti-Tau pS422 Mab to reduce Tau pathology in a mouse model of Alzheimer's Disease mice is tested by administration of the antibody to Tau.PS2APP triple transgenic mice over a period of 4 months. Thus, a group of 20 Tau.PS2APP triple transgenic mice, aged 7 months, are treated once-weekly by ip administration of murine anti-Tau pS422 Mab (clone 2.10.3). The antibody is administered at a concentration of 2 mg/ml in vehicle (20 mM histidine, 140 mM NaCl pH6.0) to give a final dose of 20 mg/kg. A second group of 20 triple transgenic mice receive an equivalent volume of vehicle. After 4 months all mice are killed and the brains removed as described in example 5. Each brain is then divided into two hemispheres, one of which is prepared for immunohistochemical analysis as described in example 5. The second hemisphere is used for quantitation of pTau levels by immunoassay as described below.

1. Extraction of Mouse Brains for Tau and pTau Assays

Brains are weighed and homogenized with a glass homogenizer in 10 volumes of ice-cold buffer comprising 25 mM TrisCl, 800 mM NaCl, 10% sucrose pH7.5. Homogenates are then centrifuged at 20,000×g. The resulting supernatants are diluted with PBS/1% BSA/1% Tween®20 at 1:100 (for Tau assays) or 1:10 (for pTau assays).

2. Tau and pTau Assays

All assays are performed using the Meso Scale Discovery® assay platform (MSD, Gaithersburg, Md., USAMD). Capture and detection antibodies are labelled with biotin and SULFO-Tag™, respectively, according to standard protocols provided by MSD. The following antibodies were used in the assays: (i) 5A6, a murine antibody directed against amino acids 19-46 in Tau, as described in Johnson, G. V. et al., J. Neurochem 68 (1997) 430-433; (ii) AT180, a murine antibody detected against pT231 in Tau [Innogenetics, Belgium]; (iii) murine anti-Tau pS422 clone 2.5.2 as described in EP1876185A1; (iv) murine anti-Tau clone 4/53 raised against full-length Tau. The antibody 5A6 is used as capture antibody, the remaining antibodies are used as detection antibodies.

96-well MSD plates coated with streptavidin are blocked for 1 h at RT with 5% BSA. Plates are washed three times with wash buffer (PBS, 0.05% Tween®20). Capture antibody, diluted in assay buffer (PBS/1% BSA/1% Tween®20) is then added and the plates incubated at 4° C. for 30 minutes. Plates are subsequently washed once. Next, 75 µl of assay buffer is added to each well, followed by 25 µl of diluted brain supernatant and 25 µl of Sulfo-tagged detection antibody. Plates are shaken at 4° C. for 1 h and subsequently washed once. Finally, 170 µl of MSD Read Buffer is added and the plates read on an MSD Sector Imager 6000.

To allow quantitation of Tau and Tau pS422 in mouse brain extracts, standard curves were constructed using Tau and Tau pS422 prepared as described in Example 2.

Lowering of the Tau pathology in the Tau.PS2APP the triple transgenic mice by chronic treatment with anti-Tau pS422 monoclonal antibody is evidenced by a reduction in typical Tau pathology observed in antibody-treated mice at 11 months of age compared to vehicle-treated mice of the same age. This reduction is manifested by the reduced neurofibrillary tangle load, as detected by immunohistochemistry, and by the reduced level of various pTau species present in brain extracts as measured by quantitative immunoassay.

Example 10

Preparation and Purification of Rabbit Antibodies a) Immunization

NZW rabbits from Charles River Laboratories International, Inc. were used for immunization. Phosphopeptide Tau (416-430)[pS422] coupled on KLH was solved in $K_3PO_4$ puffer pH 7.0 at a concentration of 1 mg/ml and mixed (1:1) with complete Freund's adjuvant (CFA) till generation of stabile emulsion. Three rabbits received an intra dermal (i.d.) injection of 2 ml of emulsion followed by a second intra muscular (i.m.) and third subcutaneous (s.c.) injection each with 1 ml in one week interval. The fourth i.m. injection of 1 ml was performed two weeks later followed by two further s.c. injections of 1 ml in four weeks interval. 10 ml peripheral whole blood samples of each animal was collected 4-6 days after third, fourth, fifth and sixth injection and used for single cell sorting in FACS. Additional 0.5 ml serum of each animal was collected at the same time and used for the determination of Tau (416-463)[pS422] specific antibody response.

b) Antibody Response

The antibody response to the immunization was determined by serial dilution of sera using an ELISA, in which 30 ng per well of biotinylated Tau (416-430)[pS422] was incubated in 1×PBS at 4° C. over night on strepatvidin pre-coated 96 wells microtiter plates (MC1347, Micro Coat Biotechnologie GmbH, Bernried, Germany). For detection, goat anti-rabbit IgG linked to a horseradish peroxidase (The Jackson laboratory) was used at 1:16000 dilution. BM Blue POD Substrat, precipitating Tetramethylbenzidine (TMB), ready-to-use solution from Roche Diagnostics GmbH was used for visualization. Reaction was stopped via 1N HCl and measured in Tecan Infinite by 450/690 nm.

c) B-cell Cloning

Coating of Plates

Sterile streptavidin-coated 6-well plates (cell culture grade) were incubated with either a mixture of 3 biotinylated control peptides (non phosphorylated Tau (416-430), MCA-K_Human (88-102)[95-pSer] and MAP2_Human (1802-1816)[pSer-1802]) or with the biotinylated phospho-peptide Tau (416-430)[pS422] each in a concentration at 0.5-1 µg/ml in PBS at room temperature for 1 h. Plates were washed in sterile PBS three times before use. Cell culture 6-well plates were coated with 2 µg/ml KLH (key hole limpet hemocyanine) in carbonate buffer (0.1 M sodium bicarbonate, 34 mM Disodiumhydrogencarbonate, pH 9.55) over night at 4 C.°. Plates were washed in sterile PBS three times before use.

Isolation of Rabbit Peripheral Blood Mononuclear Cells (PBMC)

EDTA containing whole blood was diluted twofold with 1×PBS before density centrifugation on lympholyte mammal (Cedarlane Laboratories) which was performed to isolate rabbit PBMC. PBMCs were washed twice before staining with antibodies.

EL-4 B5 Medium

RPMI 1640 (Pan Biootech, Aidenbach, Germany) supplemented with 10% FCS (Hyclone, Logan, Utah, USA), 2 mM Glutamin, 1% penicillin/streptomycin solution (PAA, Pasching, Austria), 2 mM sodium pyruvate, 10 mM HEPES (PAN Biotech, Aidenbach, Germany) and 0.05 mM beta-mercapto-ethanole (Gibco, Paisley, Scotland)

Depletion of Macrophages/Monocytes

Sterile 6-well plates (cell culture grade) were used to deplete macrophages and monocytes through unspecific adhesion. Wells were either coated with KLH (key hole limpet hemocyanine) or with streptavidin and the control peptides. Each well was filled with at maximum 4 ml medium and up to $6 \times 10^6$ peripheral blood mononuclear cells from the immunized rabbit and allowed to bind for 1 h at 37° C. in the incubator. 50% of the cells in the supernatant were used for the panning step; the remaining 50% of cells were directly subjected to immune fluorescence staining and single cell sorting.

Panning B Cells on Peptides 6-well tissue culture plates coated with strepavidin and the biotinylated peptide Tau (416-430)[pS422] were seeded with up to $6 \times 10^6$ cells per 4 ml medium and allowed to bind for 1 h at 37° C. in the incubator. Non-adherent cells were removed by carefully washing the wells 1-2 times with 1×PBS. The remaining sticky cells were detached by trypsin for 10 min at 37° C. in the incubator and then washed twice in media. The cells were kept on ice until the immune fluorescence staining.

Immune Fluorescent Staining and Single Cell Sorting

Anti-rabbit IgG FITC used for single cell sorting was from AbD Serotec (STAR121F, Düsseldorf, Germany). For surface staining, cells from the depletion and panning step were incubated with anti-rabbit IgG FITC antibody in PBS for 30 min rolling in the cold room at 4° C. in the dark. Following centrifugation, the supernatants were removed by aspiration. The PBMCs were subjected to 2 cycles of centrifugation and washing with ice cold PBS. Finally the PBMCs were resuspended in ice cold PBS and immediately subjected to the FACS analyses. Propidium iodide in a concentration of 5 µg/ml (BD Pharmingen, San Diego, Calif., USA) was added prior to the FACS analyses to discriminate between dead and live cells. FACS was performed using a Becton Dickinson FACSAria equipped the FACSDiva software (BD Biosciences, USA) and single, FITC-labeled, live cells were deposited in 96-well plates.

B Cell Culture

B cell cultures were prepared by a method similar to that described by Zubler, R. H. et al., J Immunol. 134 (1985) 3662-3668. Briefly, single sorted B cells were cultured in 96-well plates with 210 µl/well EL-4 B5 medium with Pansorbin Cells (1:20000) (Calbiochem (Merck), Darmstadt, Deutschland), 5% rabbit thymocyte supernatant and gamma-irradiated EL-4-B5 murine thymoma cells ($2 \times 10^4$/well) for 7 days at 37° C. in an atmosphere of 5% $CO_2$ in the incubator. B cell culture supernatants were removed for screening and the cells harvested immediately for variable region gene cloning or frozen at −80° C. in 100 µl RLT buffer (Qiagen, Hilden, Germany).

d) B-Cell Clone Screening

B-cell culture supernatants were screened for binding to biotinylated Tau (416-430)[pS422] by ELISA. Non-phosphorylated Tau (416-430), KLH (key hole limpet hemocyanine) and the unrelated phospho-peptide MCAK_Human (88-102)[95-pSer] were used as control antigens. For the preparation of ELISA plates, streptavidine pre-coated microtiter plates were incubated with biotinylated Tau (415-430) [pS422] at 50 ng/ml for 1 hour at room temperature. Coating with KLH or control peptides was performed at 1 µg/ml. B cell supernatants were diluted 1:5 to 1:10 and were incubated in the antigen coated microtiter plates for 60 min. After intensive washing, the binding of the rabbit antibodies was detected using a sheep anti-rabbit IgG digoxigenin conjugated detection antibody (Chemicon AQ301D). After incubation with TMB at room temperature, absorbance at 370 nm-492 nm was measured. B-cell clones yielding signals above background with biotinylated Tau (416-430)[pS422] but not with KLH and MCAK_Human (88-102)[95-pSer] were further considered and subjected to variable region gene cloning.

e) PCR Amplification of V-Domains and Sequencing

Total RNA was prepared using the NucleoSpin® 8/96 RNA kit (Macherey&Nagel; 740709.4, 740698) according to manufacturer's protocol. All steps were done on a epMotion 5075 liquid handling system (Eppendorf). RNA was eluted with 60 µl RNase free water. 6 µl of RNA was used to generate cDNA by reverse transcriptase reaction using the Superscript III First-Strand Synthesis SuperMix (Invitrogen 18080-400) and an oligo dT-primer according to the manufatures's instructions. 4 µl of cDNA were used to amplify the immunoglobulin heavy and light chain variable regions (VH and VL) with the AccuPrime Supermix (Invitrogen 12344-040) in a final volume of 50 µl using the primers rbHCfinal.up and rbHCfinal.do for the heavy chain and rbLCfinal.up and rbLCfinal.do for the light chain (Table 4). The PCR conditions were as follows: Hot start at 94° C. for 5 min; 35 cycles of 20 s at 94° C., 20 s at 70° C., 45 s at 68° C., and a final extension at 68° C. for 7 min

TABLE 4

| | |
|---|---|
| rbHCfinal.up | AAGCTTGCCACCATGGAGACTGGGCTGCGCTGGCTTC |
| rbHCfinal.do | CCATTGGTGAGGGTGCCCGAG |
| rbLCfinal.up | AAGCTTGCCACCATGGACAYGAGGGCCCCCACTC |
| rbLCfinal.do | CAGAGTRCTGCTGAGGTTGTAGGTAC |

8 µl of 50 µl PCR solution were loaded on a 48 E-Gel 2% (Invitrogen G8008-02). Positive PCR reactions were cleaned using the NucleoSpin® Extract II kit (Macherey&Nagel; 740609250) according to manufacturer's protocol and eluted in 50 µl elution buffer. 12 µl of purified PCR products were sequenced directly in both directions using the rbHCfinal.up and rbHCfinal.do for heavy chains and rbLCfinal.up and rbLCfinal.do for light chains (Table 4).

d) Recombinant Expression of Rabbit Monoclonal Antibodies and Rabbit/Mouse Chimeric Antibodies For recombinant expression of rabbit monoclonal antibodies, PCR-products coding for VH or VL were cloned as cDNA into expression vectors by the overhang cloning method (Haun, R. S. et al., Biotechniques 13 (1992) 515-518; Li, M. Z., et al., Nature Methods 4 (2007) 251-256). Linearized expression plasmids coding for the rabbit kappa or gamma constant region and VL of VH inserts were amplified by PCR using overlapping primers. Purified PCR products were incubated with T4 DNA-polymerase which generated single-strand overhangs. The reaction was stopped by dCTP addition. In the next step, plasmid and insert were combined and incubated with recA which induced site specific recombination. The recombined plasmids were transformed into E. coli. The next day the grown colonies were picked and tested for correct recombined plasmid by plasmid preparation, restriction analysis and DNA-sequencing. For antibody expression, the isolated HC and LC plasmids were transiently co-transfected into HEK293 cells and the supernatants were harvested after 1 week. For cloning and expression of rabbit mouse chimeric antibodies, the VH and VL regions were amplified by PCR and sub-cloned into expression vectors containing the mouse constant kappa or mouse constant gamma 1 region. The rabbit/mouse chimeric HC and LC plasmids were isolated, tested by restriction analysis and DNA-sequencing for correct insertion and transiently co-transfected into HEK293 cells. Supernatants were harvested one week after transfection.

e) Antibody Purification

Recombinantly expressed rabbit antibodies were purified from cell culture supernatants on MabSelectSuRe™ columns (GE Healthcare). Prior to sample load the column was equilibrated with 25 mmol/L Tris-HCl, 25 mmol/L NaCl, pH 7.4. Elution of the antibody was achieved with 50 mmol/L acetate pH 3.14. The eluted sample was immediately loaded onto a desalting column (Sephadex G25, GE Healthcare) and eluted in 20 mmol/L His-HCl, 140 mmol/L NaCl pH 6.0. This buffer was also used for the storage of purified antibody. General storage temperature was 4° C., room temperature during the purification process and −80° C. after aliquotation. Recombinantly expressed rabbit/mouse chimaeras antibodies from cell culture supernatants were purified on MabSelectSuRe™ columns (GE Healthcare). Prior to sample load the column was equilibrated with 1×PBS, pH 7.4. Elution of the antibodies was achieved with 100 mmol/L citrate pH 3.0. The eluted sample was immediately neutralized with 2 mol/L Tris/HCl pH 9.0. Afterwards the antibodies are loaded onto a size exclusion column (Superdex 200, GE Healthcare) and eluted in 20 mmol/L His-HCl, 140 mmol/L NaCl pH 6.0 This buffer was also used for the storage of purified antibodies. General storage temperature was 4° C., room temperature during the purification process and −80° C. after aliquotation.

Example 11

Anti-Tau pS422 Mononoclonal Rabbit Antibodies are Highly Selective for Tau Phosphorylated at pS422 and Bind to Fibrillary Aggregates of Tau pS422 a) ELISA

Rabbit monoclonal antibodies were recombinantly expressed in HEK 293 cells. Cell culture supernatants or purified rabbit antibodies were tested for binding to biotinylated Tau (416-430)[pS422], non-phosphorylated Tau (416-430), KLH (key hole limpet hemocyanine) and the unrelated phospho-peptide MCAK_Human (88-102)[95-pSer] by ELISA. For the preparation of ELISA plates, streptavidine pre-coated microtiter plates were incubated with biotinylated Tau (415-430)[pS422] at 50 ng/ml for 1 hour at room temperature. Coating with KLH or control peptides was performed at 1 µg/ml. Rabbit Anti Tau pS422 antibody (Abcam AB51071) or rabbit antibody containing supernatants were incubated in the antigen labeled microtiter plates for 60 min at various concentrations. After intensive washing, the binding of the rabbit antibodies was detected using a sheep anti-rabbit IgG digoxigenin conjugated detection antibody (Chemicon AQ301D). After incubation with TMB at room temperature absorbance at 370 nm-492 nm was measured. The antibody binding was characterized by its EC50 values. The antibody binding to biotinylated Tau (416-430)[pS422] and non-phosphorylated Tau (416-430) peptides was characterized by its EC50 values. Cross-reactivity with KLH or MCAK phosphopeptide was estimated by single-point measurement at high concentrations, i.e. at 1:5 dilution of the cell culture supernatants. Results are shown in table 5. EC50 values of binding to Tau phosphopeptide were found to be more than 100 times lower than EC50 values of binding to Tau peptide, indicating at least 100 fold selectivity for phosphorylated Tau fragment compared to non-phosphorylated Tau peptide. Binding to KLH and MCAK control phosphopeptide was at background level with all antibodies, which is about 1<3% of the maximal value measures with Tau phosphopeptide.

TABLE 5

|  | EC50 phosphorylated Tau peptide (µg/ml) | EC50 non-phos-phorylated Tau peptide (µg/ml) | IgG titer of supernatant (µg/ml) | OD 1:5 dilution of supernatant | |
|---|---|---|---|---|---|
|  |  |  |  | KLH (mE) | MCAK (mE) |
| Mab 005 | <0.003 | 3.727 | 5.818 | 0.026 | 0.067 |
| Mab 019 | <0.003 | 1.076 | 6.958 | 0.026 | 0.023 |
| Mab 020 | 0.002 | >3.369 | 3.369 | 0.016 | 0.010 |
| Mab 085 | 0.0009 | 0.146 | 6.46 | 0.029 | 0.062 |
| Mab 086 | 0.0011 | 0.266 | 8.84 | 0.046 | 0.104 |
| Mab 097 | 0.0013 | 1.281 | 19.87 | 0.042 | 0.029 |

Specificity for soluble and aggregated full-length Tau pS422 was also tested. Fibrillary aggregates of Tau pS422 (300 µg/ml) were coated to a Polystyrene based MaxiSorb mircotiter plate (Nunc) overnight at RT. In similar manner, soluble full-length Tau and Tau pS422 were coated to the MaxiSorb microtiter plate. Rabbit Anti Tau pS422 antibody control (Abcam AB51071), or purified rabbit antibodies were added and incubated for 60 min in concentrations up to 1000 ng/ml. After intensive washing, the binding of the rabbit antibodies was detected using a sheep anti-rabbit IgG digoxigenin conjugated detection antibody (Chemicon AQ301D). After incubation with TMB at room temperature absorbance at 370 nm-492 nm was measured. The antibody binding was characterized by its EC50 values. Results are shown in Table 6.

TABLE 6

| Rabbit Mab | EC50 Tau pS422 protein (µg/ml) | EC50 Tau protein (µg/ml) | EC50 fibrillary Tau pS422 (µg/ml) |
|---|---|---|---|
| Mab 005 | 0.00034 | no binding | 0.00755 |
| Mab 019 | 0.00038 | no binding | 0.00059 |
| Mab 020 | 0.00036 | no binding | 0.00042 |
| Mab 085 | 0.00025 | no binding | 0.00074 |
| Mab 086 | 0.00023 | no binding | 0.00048 |
| Mab 097 | 0.00040 | no binding | 0.01358 |

Rabbit monoclonal antibodies bound to Tau-pS422 protein with EC50 values below 1 ng/ml. Fibrillary Tau pS422 was detected with EC50 values ranging from 0.4 ng/ml to 14 ng/ml. Signals for binding to non-phosphorylated full-lengths Tau protein were indistinguishable from background levels. Therefore it was estimated that each of the antibodies binds to Tau pS422 and fibrillary Tau pS422 with a selectivity of at least 100-fold compared to Tau.

b) Biacare™

Binding to fibrillary Tau pS422 aggregates was further investigated and confirmed by BIAcore™ analysis. Measurements were performed using the BIAcore 3000™ instrument at 37° C. The system and sample buffer was HBS-EP (10 mM HEPES, 150 mM NaCl, 3.4 mM EDTA, 0.005% Polysorbate 20 (v/v)). A BIAcore™ CM5 sensor chip was subjected to a preconditioning procedure. Sequentially 0.1% SDS, 50 mM NaOH, 10 mM HCl and 100 mM $H_3PO_4$ were injected for 30 sec over the flow cells FC1, FC2, FC3 and FC4. The amine coupling procedure was done according to the manufacturers instructions using the BIAcore 3000™ wizard v. 4.1. After an EDC/NHS activation of the sensor surface, a non-phospho-selective anti-Tau antibody mAb <TAU>M-4/53-IgG was immobilized on sensor flow cells FC2, FC3 and FC4. As a control, an antibody against CK-MM (creatine kinase isotype), recognizing an irrelevant antigen, was captured on the FC1. mAb <TAU>M-4/53-IgG and the antibody against CK-MM were diluted at 30 µg/ml in 10 mM NaAc pH 5.0 and were injected at 10 µl/min for 7 min contact time to immobilize 10.000 RU of the antibody capturing system. The surface was deactivated by saturation with 1M Ethanolamine. The sensor was conditioned by 5 cycles with phosphorylated filamentous Tau protein (stock 0.3 mg/ml diluted 1:100 in HBS-EP) as analyte in solution at 10 µl/min for 2 min Regeneration was performed with 10 mM Glycine pH 2.5 at 30 µl/min for 3 min. It is assumed, that the analyte binding to mAb 4/53 does not dissociate the pTau filaments, because no dissociation of pTau filaments from the mAb 4/53 could be observed. For all further measurement cycles, 0.3 mg/ml pTau filaments were diluted 1:100 in HBS-EP buffer and were injected at 10 µl/min for 1 min in order to present pTau to the respective antibody analytes in a heterogeneous sandwich-mode. The antibody analytes were diluted in HBS-EP buffer to a concentration of 100 nM and were injected into the system at 20 µl/min for 3 min. After 3 min of dissociation the sensor surface was regenerated by 2 injections of a 10 mM Glycine pH 2.5 for 1 min at 100 µl/min followed by a HBS-wash for 15 sec at 100 µl/min. The association and dissociation phase of the interactions were monitored. Since the antibody analyte in solution is bivalent, the avidity-burdened antibody-pTAU kinetics were characterized by a biphasic dissociation model, consisting of a fast affinity-based early dissociation step followed by an avidity-stabilized, but rate-limiting kinetic step in the latter complex dissociation. 10 sec (early) and 50 sec (late) after analyte injection end, the kd and t/2 diss were quantified, where possible. The kinetic measurements were evaluated using a double referencing procedure. First the signal from the FC1 reference was subtracted to correct the buffer bulk effect and unspecific binding. Second the 0 nM analyte injection was subtracted to correct the dissociation of the primary antibodies from the respective capturing system. The kinetic rates were evaluated using a Langmuir 1.1 dissociation fit model according to the Biacore™ evaluation software v.4.1. The antigen/antibody complex stability halftime (mM) was calculated according to the formula ln(2)/60*kd.

Results are summarized in Table 7.

TABLE 7

| Clone | early (10 s) | | late (50 s) | |
|---|---|---|---|---|
| | kd (1/s) | t/2diss (min) | kd (1/s) | t/2diss (min) |
| Mab 005 | 2.19E−03 | 5.3 | $3.12 \times 10^{-3}$ | 4 |
| Mab 019 | 1.43E−02 | 0.8 | $6.17 \times 10^{-4}$ | 19 |
| Mab 020 | 3.28E−03 | 3.5 | $4.08 \times 10^{-4}$ | 28 |
| Mab 085 | n.d. | n.d. | $6.60 \times 10^{-4}$ | 18 |
| Mab 086 | 1.62E−03 | 7.2 | $3.68 \times 10^{-4}$ | 32 |
| Mab 097 | n.d. | n.d. | n.d. | n.d. |

Example 12

Binding of Anti-Tau pS422 Monoclonal Rabbit Antibodies to Intracellular pTau in Brain Sections of Alzheimer's Disease Patients The specific and sensitive immunohistochemical detection of pTau pathology in Alzheimer's disease brain tissue by monoclonal rabbit anti-Tau pS422 antibodies was investigated by immunofluorescence staining experiments using cryosections of human brain tissue from AD patients. The procedure was basically the same as described in example X (murine antibodies). Rabbit IgGs were detected by goat anti rabbit Alexa Fluor® 488 conjugated secondary antibodies (Invitrogen/MolecularProbes A11034). Specific and sensitive staining of pTau deposits and filaments is evident for clones Mab 005, Mab 019, Mab 020, Mab 085, Mab 086 and Mab 097. Intracellular pTau deposits, like large neurofibrillary tangles and elongated neuropil threads, are noticeable. A minimal effective concentration ranging between 0.08 and 0.016 µg/ml was determined for all clones investigated, which indicates highly sensitive binding to genuine human pTau deposits.

The invention claimed is:

1. An antibody, which specifically binds to Tau phosphorylated at serine 442 (Tau pS422) and to the phosphorylated Tau fragment of SEQ ID NO:9 but does not bind to either wild-type Tau or to the phosphorylated human mitotic centromere-associated kinesin (MCAK) fragment of SEQ ID NO:17, and which comprises the complementary determining regions (CDRs): CDR1H of SEQ ID NO:55, CDR2H of SEQ ID NO:56, CDR3H of SEQ ID NO:57, CDR1L of SEQ ID NO:59, CDR2L of SEQ ID NO:60, and CDR3L of SEQ ID NO:61, wherein the antibody is a variant antibody that has been humanized.

2. An antibody, which specially binds to Tau pS422 and to the phosphorylated Tau fragment of SEQ ID NO:9 but does not bind to either wild-type Tau or to the phosphorylated MCAK fragment of SEQ ID NO:17, and which comprises a variable light chain of SEQ ID NO:58 and a variable heavy chain of SEQ ID NO:54, wherein the antibody is a variant antibody that has been humanized.

* * * * *